United States Patent [19]

Wagner et al.

[11] 4,294,719
[45] Oct. 13, 1981

[54] POLYISOCYANATES WHICH CONTAIN CARBODIIMIDE GROUPS AND WHICH ARE STABLE IN STORAGE

[75] Inventors: Kuno Wagner, Leverkusen; Hans-Dieter Block; Walter Schäfer, both of Cologne, all of Fed. Rep. of Germany

[73] Assignee: Bayer Aktiengesellschaft, Leverkusen, Fed. Rep. of Germany

[21] Appl. No.: 822,489

[22] Filed: Aug. 8, 1977

Related U.S. Application Data

[63] Continuation of Ser. No. 653,689, Jan. 30, 1976, abandoned.

[30] Foreign Application Priority Data

Feb. 1, 1975 [DE] Fed. Rep. of Germany ....... 2504400

[51] Int. Cl.³ .................. C08G 18/18; C08G 73/10
[52] U.S. Cl. ..................................... 252/182; 528/44; 528/67
[58] Field of Search ................. 252/182; 528/67, 44

[56] References Cited

FOREIGN PATENT DOCUMENTS

| 899036 | 6/1962 | United Kingdom . |
| 951505 | 3/1964 | United Kingdom . |
| 1083410 | 9/1967 | United Kingdom . |
| 1115260 | 5/1968 | United Kingdom . |
| 1200432 | 7/1970 | United Kingdom . |

Primary Examiner—Benjamin R. Padgett
Assistant Examiner—Irwin Gluck
Attorney, Agent, or Firm—Gene Harsh; Joseph C. Gil; R. Brent Olson

[57] ABSTRACT

The present invention relates to stable equilibrium mixtures of carbodiimides, uretone imines and organic isocyanates and to stable solutions of carbodiimides and uretone imines in polyisocyanates which are free from carbodiimide groups. Either the carbodiimide, or the uretone imine, or both, may contain isocyanate groups. The present invention also relates to a process for the preparation of such products by "heterogeneous catalysis" and the use thereof for the production of polyurethane resins. According to one embodiment of the process according to the instant invention, individual isocyanates in a mixture of various isocyanates may be carbodiimidized selectively.

19 Claims, 2 Drawing Figures

POLYISOCYANATES WHICH CONTAIN CARBODIIMIDE GROUPS AND WHICH ARE STABLE IN STORAGE

This is a continuation of application Ser. No. 653,689 filed Jan. 30, 1976 now abandoned.

BACKGROUND OF THE INVENTION

Carbodiimides may be prepared from isocyanates by a particularly simple reaction even at room temperature based on a process described in German Pat. No. 1,130,594 in which phospholine oxides are used as catalysts. Industrially the most important and effective catalysts which effect very rapid carbodiimidization of virtually any aromatic monoisocyanate and polyisocyanate even at room temperature and are capable of converting less reactive aliphatic or cycloaliphatic monoisocyanates and polyisocyanates into carbodiimides at temperatures starting from about 150° C. are those corresponding to the general formulae:

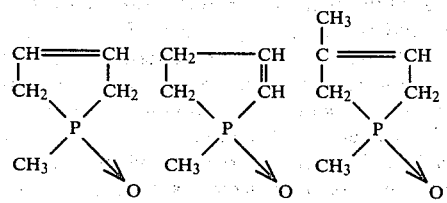

These catalysts have been used commercially for the production of polycarbodiimide foams.

Experience has shown that carbodiimide formation with the aid of the above-mentioned readily soluble catalysts, which formation proceeds in the form of a homogeneous catalysis, cannot be stopped in such a way that carbodiimides or polycarbodiimides which contain isocyanate groups are obtained as reaction products which are stable in storage. It is likewise not possible to prepare stable solutions of diisocyanatocarbodiimides, such as

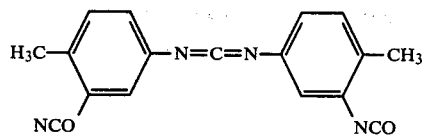

or α,ω-diisocyanato-bis-carbodiimides, α,ω-diisocyanato-tris-carbodiimides or isocyanato-uretone imines such as those corresponding to the formula:

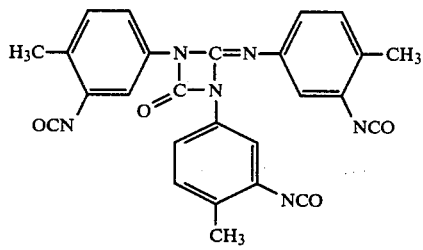

in excess monomeric monoisocyanates or polyisocyanates. The reason for this failure in the art is that the catalytically highly active soluble phospholine oxides cannot be completely blocked by any of the known inactivating agents, such as phosphorus oxychloride, zinc chloride, dimethyl carbamic acid chloride, benzoyl chloride, hydrochloric acid, boron trifluroide, alkylating agents and the like. Neither the formation of carbodiimides nor the polymerization to polycarbodiimides and crosslinked products can therefore be completely stopped. Thus, because of the progressive (even though in some cases, slow) formation of carbodiimide, a high carbon dioxide pressure soon develops in closed reaction and/or storage vessels which may result in serious accidents.

DESCRIPTION OF THE INVENTION

Figure 1:
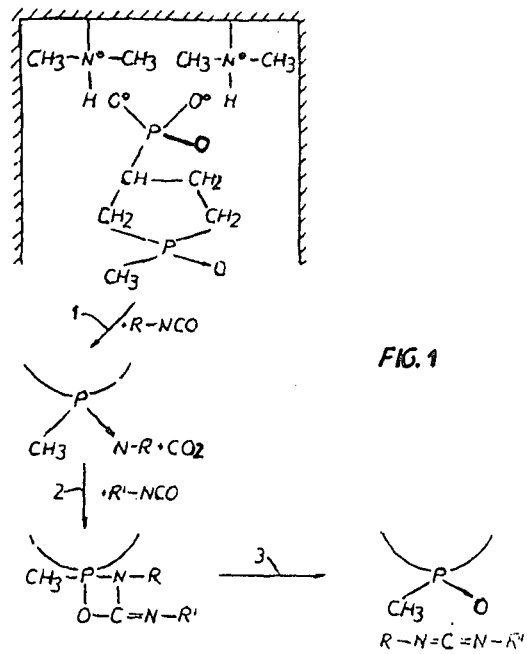
FIG. 1 represents the reaction scheme believed to occur during the process of the instant invention.

It has now surprisingly been found that carbodiimidization catalysts may be bound to an insoluble high molecular weight inorganic or organic matrix via ionic bonds without substantial reduction of their catalytic activity. High molecular weight, insoluble catalysts are thereby obtained which may be removed from the reaction mixture at any time so that it is now possible to convert monoisocyanates and, preferably, polyisocyanates into stable carbodiimides or polycarbodiimides which contain functional NCO-groups. It is also possible to produce stable mixtures of (poly) carbodiimides and polyisocyanates. One particularly surprising finding is that it is even possible to carry out selective carbodiimidization of certain monoisocyanates or polyisocyanates of an isocyanate mixture.

The present invention therefore relates to equilibrium mixtures which are free from catalyst and stable in storage, and which comprise an organic carbodiimide, an organic uretone imine and an organic isocyanate. The organic isocyanate may be a carbodiimide and/or a uretone imine containing an isocyanate group or groups. Alternatively, the organic isocyanate may be present as a mono and/or polyisocyanate which is free from carbodiimide and uretone imine groups. The present invention also relates to a process for the preparation of the mixtures according to the invention, which process is characterized in that mono- and/or polyisocyanates, optionally in the presence of inert organic solvents, are brought into contact with high molecular weight, insoluble catalysts consisting of a high molecular weight, insoluble, inorganic or organic matrix and low molecular weight carbodiimidization catalysts linked to this matrix by means of ionic bonds. The high molecular weight, insoluble catalyst is removed when the desired degree of carbodiimidization has been reached and, if desired, mono- and/or poly-isocyanates which are free from carbodiimide groups are subsequently added. In selecting any particular high molecular weight inorganic or organic matrix, it is only necessary that the matrix be insoluble in the reactants, water and any organic solvents optionally used.

In addition, the invention relates to the use of the mixtures according to the invention which contain isocyanate groups and, in equilibrium, both carbodiimide groups and uretone imine groups, for the production of polyurethane resins.

The ionic bond between the high molecular weight matrix and low molecular weight carbodiimidization catalyst is preferably brought about by basic groups built into the matrix and acid groups built into the catalyst. The high molecular weight carrier materials used may be, for example, any inorganic or organic anion exchangers of the type described in the literature, for example in Houben Weyl, Volume I/1, Allgemeine Laboratoriumpraxis (1958), pages 525-532. Suitable inorganic carrier materials include skapolythes, hydroxyl apatites, iron oxide gels and the like. Preferred organic carrier materials are cross-linked polymers or copolymers of styrene containing basic groups, of the type generally known and used in the art as anion exchangers. In general, however, it is suitable to use any high molecular weight, insoluble organic carrier material which has been prepared by polymerization or polycondensation reactions and which contains basic groups, such as for example, those of the following formulae:

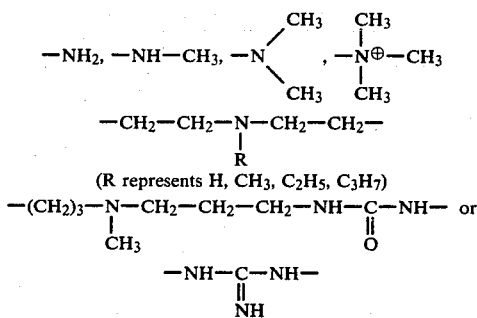

High molecular weight organic carrier materials of various chemical compositions which contain such basic groups will be described in detail in the Examples. Several commercial anion exchangers suitable for the process according to th4 invention are listed in Table 1. Additionally, much literature has been generated relative to the anion exchangers known in the art. Typical of such literature are U.S. Pat. Nos. 3,006,866 and 3,725,313, the disclosures of which are incorporated by reference.

Basic carrier materials suitable for the purpose of the invention also include polyethylene imines which have been cross-linked, for example, with 1,4-bis-(chloromethyl)-benzene, such as those described in "Die makromolekulare Chemie"128 (1969), 229-235 (No. 3141).

The preferred carrier materials consist of polystyrene which has been cross-linked with from 2 to 6%, by weight, and preferably from 4 to 5%, by weight, of divinyl benzene.

The carrier materials preferably contain from about $20.5 \times 10^{17}$ to $10.3 \times 10^{17}$ of the above-mentioned basic groups per milligram of the carrier material.

It is, of course, also possible to utilize acidic carrier materials of the type known in the art provided that the carbodiimidization catalyst used is of a basic nature.

Inert solvents which may optionally be present during the process according to the invention must not contain any functional groups which are reactive towards isocyanates. Examples of such solvents are optionally halogenated aliphatic and aromatic hydrocarbons, e.g. toluene, benzene, xylene, chlorobenzene, heptane and tetrachloromethane, ketones such as methyl ethyl ketone and cyclohexanone, ethers such as diisopropyl ether and dioxane and amides, e.g. dimethyl formamide and dimethyl acetamide.

TABLE 1

| Matrix | ionic group | grain structure | grain size (mm) | bulkweight (g/l of resin after swelling) | Total capacity (m val/ml of resin after swelling) |
|---|---|---|---|---|---|
| Polystyrene containing divinyl benzene (prepared by introducing the ionic groups according to Example 5 into the polystyrene resin of Example 2 of U.S. Pat. No. 3,006,866) | $-\overset{\oplus}{N}(CH_3)_2CH_2CH_2OH$ | macroporous | 0.3-1.5 | 660-700 | 1.2 |
| Polystyrene containing divinyl benzene (prepared according to Example 6 of U.S. Pat. No. 3,006,866, but containing only 5% by weight of divinyl benzene) | $-\overset{\oplus}{\underset{H}{N}}-(CH_3)_2$ | macroporous | 0.3-1.5 | 600-700 | 1,9 |
| Polystyrene containing divinyl benzene (prepared according to Example 2 of U.S. Pat. No. 3,006,866) | $\overset{\oplus}{N}(CH_3)_3$ | macroporous | 0.3-1.5 | 650-700 | 1.2 |
| Polystyrene containing divinyl benzene (prepared according to Example 6 of U.S. Pat. No. 3,006,866, wherein the amine groups are only quaternized to an extent of 10%) | $-\overset{\oplus}{\underset{H}{N}}-(CH_3)_2$ | macroporous | 0.3-1.2 | 600-700 | 1.5 |
| Polycondensate of epichlorohydrin and triethylene tetramine (prepared according to U.S. Pat. No. 3,725,313) | $-\overset{\oplus}{N}R_2H$ and $-\overset{\oplus}{N}R_3$ | in the form of a gel | 0.3-1.2 | approx. 700 | 2.2 |

TABLE 1-continued

| Matrix | ionic group | grain structure | grain size (mm) | bulkweight (g/l of resin after swelling) | Total capacity (m val/ml of resin after swelling) |
|---|---|---|---|---|---|
| Polystyrene containing divinyl benzene (prepared according to Example 1 of U.S. Pat. No. 3,006,866, but containing only 5% by weight of divinyl benzene) | $\overset{\oplus}{N}(CH_3)_3$ | no macropores | 0.3–1.2 | 680–750 | 1.6 |
| Polystyrene containing divinyl benzene (prepared according to Example 2 of Pat. No. 3,006,866, but without using the white spirit and containing only 5% of divinyl benzene) | $-\overset{\oplus}{N}(CH_3)_3$ | no macropores | 0.3–1.2 | 700–750 | 1.3 |

The low molecular weight carbodiimidization catalyst which is to be fixed to the high molecular weight matrix must carry groups of opposite charge to that of the matrix. In principle, any known carbodiimidization catalyst which has been modified by the incorporation of at least one ionic group is suitable. As explained above, it is preferred to use catalysts which contain acid groups, for example carboxylic, sulphonic, phosphinic acid groups, and the like. Cyclic phosphine oxides modified with phosphonic, thiophosphonic or phosphinic acid groups are particularly preferred for the invention owing to their ready availability.

Compounds of this type correspond to the following general formula:

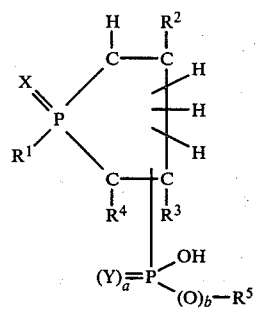
(I)

wherein
  $R^1$ represents an alkyl or aryl group which contains up to 14 carbon atoms;
  $R^2$, $R^3$ and $R^4$ each represent a $C_1$–$C_4$ alkyl group, hydrogen, chlorine or bromine;
  $R^5$ represents hydrogen, a $C_1$–$C_{12}$ alkyl group and, if b=0, a $C_6$–$C_{12}$ aryl group;
  X and Y represent oxygen or sulphur; and
  a and b=0 or 1.

Compounds of this type are relatively easily prepared by reacting 5-membered cyclic phosphine oxides corresponding to the general formulae:

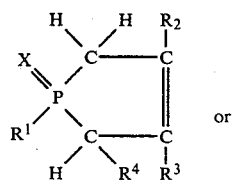
(II)

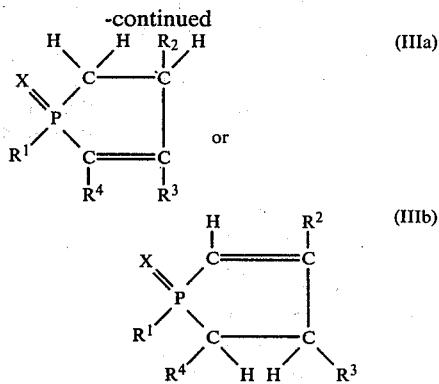
(IIIa)

or (IIIb)

wherein $R^1$, $R^2$, $R^3$, $R^4$ and X are as defined above with compounds of the following general formula which contain phosphorus-hydrogen bonds:

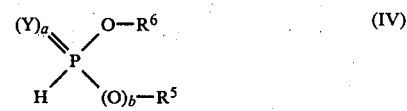
(IV)

wherein a, b, $R^5$ and Y are as defined above and $R^6$ represents an alkyl group or hydrogen. The reaction is conducted in the presence of known radical initiators or high energy radiation at temperatures of from about 50° to about 300° C., optionally followed by saponification.

Starting materials corresponding to the general structural formulae (II) and (III) are known and may be prepared by known methods (see G. M. Kosolapoff, L. Maier, Organic Phosphorus Compounds, Wiley-Interscience, New York, 1972, Volume 3, and pages 370–371 and pages 458–463 and Volume 4, pages 9–10 and page 48). Aminophospholanes and aminophospholine oxides may also be used (see Kosolapoff, supra). Such compounds may correspond to the following formula:

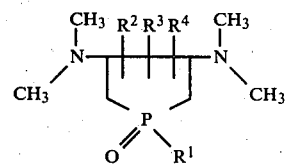

wherein R¹ to R⁵ are as defined above. The following are examples of 5-membered, unsaturated phosphine oxides, in which the double bond may be either in the 2,3-position or in the 3,4-position:

1-methyl-1-oxophospholine,
1-ethyl-1-oxophospholine,
1-butyl-1-oxophospholine,
1(2-ethylhexyl)-1-oxophospholine,
1-methyl-1-thiophospholine,
1-(2-chloroethyl)-1-oxophospholine,
1-phenyl-1-oxophospholine,
1-p-tolyl-1-oxophospholine,
1-chloromethyl-1-oxophospholine,
1,3-dimethyl-1-oxophospholine,
1,2-dimethyl-1-oxophospholine,
1-methyl-3-chloro-1-oxophospholine,
1-methyl-1-bromo-1-oxophospholine,
1-chlorophenyl-1-oxophospholine,
1,3,4-trimethyl-1-oxophospholine,
1,2,4-trimethyl-1-oxophospholine,
1,2,2-trimethyl-1-oxophospholine,
1-phenyl-1-thiophospholine,
1-phenyl-3-methyl-1-oxophospholine and 1-phenyl-2,3-dimethyl-1-oxophospholine.

Th following are examples of phosphorus-hydrogen compounds which may be used according to the invention:

dimethyl phosphite,
diethyl phosphite,
diisopropyl phosphite,
di-n-propyl phosphite,
di-isobutyl phosphite,
di-n-octyl phosphite,
di-decyl phosphite and
methyl-ethyl phosphite,
methane phosphonous acid methyl ester,
methane phosphnous acid ethyl ester,
methane phosphonous acid n-butyl ester,
ethane phosphonous acid methyl ester,
ethane phosphonous acid 2-ethylhexyl ester,
benzene phosphonous acid methyl ester,
benzene phosphonous acid isopropyl ester,
dimethyl phosphine oxide,
methylethyl phosphine oxide,
di-n-butyl phosphine oxide,
methyl-phenyl phosphine oxide,
diphenyl phosphine oxide,
dimethyl thiophosphite,
diethyl thiophosphite,
di-isobutyl-thiophosphite,
methane thiophosphonous acid methyl ester and
dimethyl phosphine sulphide,
dimethyl phosphine,
diethyl phosphine,
diphenyl phosphine,
methylphenyl phosphine,
dibutoxy phosphine,
methyl phosphine,
ethyl phosphine and
phenyl phosphine.

The reaction may be initiated by radical forming substances which are active at temperatures of from about 50° to 300° C., such as organic peroxides and aliphatic azo compounds, as well as by high-energy radiation. The following are examples of suitable radical forming agents: dialkyl peroxides, such as di-tert.-butyl peroxide; diacyl peroxides, such as dibenzoyl peroxide, p-chlorobenzoyl peroxide, 2,4-dichlorobenzoyl peroxide, succinyl peroxide, nonanoyl peroxide and lauroyl peroxide; peroxy esters, such as tert.-butyl peroctoate, tert.-butyl perisobutyrate, tert.-butyl peracetate, tert.-butyl perbenzoate and tert.-butyl perpivolate; peroxyketals and percarbonates; azoisobutyric acid nitrile, and azo-bis-isobutanoldiacetate, as well as UV radiation, X-rays and gamma rays. Other, equivalent radical-forming agents as well known to those skilled in the art and their suitability may easily be ascertained by simple perliminary tests if necessary.

The reaction between the starting materials is generally carried out by adding the 5-membered unsaturated phosphine oxide dropwise to the phosphorus-hydrogen compound in a molar ratio of from about 1:0.1 to 1:1. No solvents are required, but an inert solvent may be used if desired. The radical-forming agent is used in a quantity of from 0.1 to 20 mol-%, preferably from 0.5 to 5 mol-%, based on the 5-membered, unsaturated cyclic phosphine oxide, and it is added to the reaction mixture together with the said phosphine oxide. Before the radical-forming agent is added, it may be dissolved in an inert solvent or in one of the reactants. Alternatively, the reactants may be mixed together, with or without radical-forming agent, and the mixture may then be heated to the reaction temperature. When this temperature is reached, the radical-forming agent, which must have a sufficiently short half-life period at this temperature, is intermittently added portionwise to the mixture.

The reaction temperatures employed are from about 50° to about 300° C., and preferably from 100° to 200° C. The reaction generally takes from about 0.5 to about 30 hours, depending on the size of the batch and the conditions employed. The reaction time, however, may vary within wide limits.

The reaction is preferably carried out at normal pressure although elevated or reduced pressure may be employed. The atmosphere under which it is carried out may be air or inert gas.

The reaction products are subsequently partially or completely saponified (as, for example, shown in the Examples) and then applied to the insoluble, high-molecular weight matrix which contains basic groups, where they are fixed with the formation of ionic bonds. Since the acid-substituted phospholine oxides are water-soluble, the matrix may very easily be charged with catalyst molecules by stirring in an aqueous medium or continuously on a column.

The compounds particularly preferred according to the invention are the isomeric 1-methyl-1-oxo-phospholanephosphonic acids, 1-methyl-1-oxo-phospholane-phosphinic acid, 1-methyl-1-thio-phospholane-phosphonic acids and 1-methyl-1-oxo-phospholane-thiophosphonic acids.

According to the invention any aliphatic, cycloaliphatic, araliphatic, aromatic or heterocyclic polyisocyanate, such as those described, for example, by W. Siefken in Justus Liebigs Annalen der Chemie, 562, pages 75–136 may be carbodiimidized. Examples include ethylene diisocyanate; tetramethylene-1,4-diisocyanate; hexamethylene-1,6-diisocyanate; dodecane-1,12-diisocyanate; cyclobutane-1,3-diisocyanate; cyclohexane-1,3- and -1,4-diisocyanate and mixtures of these isomers; 1-isocyanato-3,3,5-trimethyl-5-isocyanatomethyl-cyclohexane (German Auslegeschrift 1,202,785 and U.S. Pat. No. 3,401,190); hexahydrotolylene-2,4- and -2,6-diisocanate and mixtures of these isomers; hexahydrophenylene-1,3- and/or -1,4-diisocyanate; perhydrodipheylmethane-2,4'- and/or -4,'- diisocyanate; phenylene-1,3- and -1,4-diisocyanate; tolylene-2,4- and -2,6-diisocyanate and mixtures of these isomers; diphenylmethane-2,4'- and/or4,'-diisocyanate; naphthylene-1,5-diisocyanate; triphenylmethane-4,4', 4''-triisocyanate; polyphenyl-polymethylene polyisocyanates of the type which may be obtained by anilineformaldehyde condensation followed by phosgenation and which have been described, for example, in British Pat. Nos. 874,430 and 848,671; m- and p-isocyanatophenylsulphonyl isocyanates as described in U.S. Pat. No. 3,454,606; perchlorinated aryl polyisocyanates as described in U.S. Pat. No. 3,277,138; polyisocyanates which contain carbodiimide groups as described in U.S. Pat. No. 3,152,162; the diisocyanates described in U.S. Pat. No. 3,492,330; polyisocyanates which contain allophanate groups as described in British Pat. No. 994,890, Belgian Pat. No. 761,626 and published Dutch Patent Application No. 7,102,524; polyisocyanates which contain isocyanurate groups as described in U.S. Pat. No. 3,001,973, German Pat. Nos.1,022,789; 1,222,067 and 1,027,394, and in German Offenlegungsschrift Nos. 1,929,034 and 2,004,048; polyisocyanates which contain urethane groups as described in Belgian Pat. No. 752,261 or in U.S. Pat. No. 3,394,164; polyisocyanates which contain acylated urea groups as described in German Pat. No. 1,230,778; polyisocyanates which contain biuret groups as described in U.S. Pat. Nos. 3,124,605 and 3,201,372 and in British Pat. No. 889,050; polyisocyanates prepared by telomerization reactions as described in U.S. Pat. No. 3,654,106; polyisocyanates which contain ester groups as described in British Pat. Nos. 965,474 and 1,072,956, in U.S. Pat. No. 3,567,763 and in German Pat. No. 1,231,688; reaction products of the above-mentioned isocyanates with acetals as described in German Pat. No. 1,072,385; and polymeric polyisocyanates which contain fatty acid groups as described in U.S. Pat. No. 3,455,883.

The distillation residues which still contain isocyanate groups from the commercial production of isocyanates may also be used, if desired as solutions in one or more of the above-mentioned polyisocyanates. Mixtures of the above-mentioned polyisocyanates may also be used.

The following aromatic polyisocyanates are preferred according to the invention: tolylene-2,4-diisocyanate; tolylene-2,6-diisocyanate and mixtures of these isomers; m-phenylene diisocyanate; p-phenylene diisocyanate; and, from approximately 10 to 40%, by weight, solutions of biuretization, allophanatization, urethanization, trimerization and dimerization products of these polyisocyanates in monomeric polyisocyanates, particularly in monomeric tolylene diisocyanate.

Mixtures of the above-mentioned monomeric polyisocyanates, in particular of tolylene diisocyanate, with from approxiamtely 5 to 95%, by weight, of 4,4'-diisocyanatodiphenylmethane, which mixtures may be carbodiimidized selectively without reaction of 4,4'-diisocyanatodiphenylmethane diisocynate, are also preferred. Even small proportions of the carbodiimidized tolylene diisocyanate have the unexpected effect of converting 4,4'-diisocyanatodiphenylmethane, which, crystallizes at room temperature, into a liquid mixture which is stable in storage.

Amomg the aliphatic, cycloaliphatic and araliphatic polyisocyanates, it is preferred to use tetramethylene diisocyanate, pentamethylene diisocyanate, hexamethylene diisocyanate, dicyclohexylmethane diisocyanate, 1-isocyanato-3,3,5-trimethyl-5-isocyanatomethyl cyclohexane, lysine ester diisocyanates and m-and p-xylene diisocyanates or solutions or their biuretization and dimerization products in the corresponding monomeric polyisocyanates. Again, due to the selective action of the catalysts, practically no carbodiimidization of the higher molecular weight components takes place and consequently crosslinking reactions and the attendant high increases in viscosity do not occur.

Monoisocyanates may, of course, also be carbodiimidized. Suitable monoisocyanates include methyl isocyanate, ethyl isocyanate, propyl isocyanate, isopropyl isocyanate, n-butyl isocyanate, n-hexyl isocyanate, $\omega$-chlorohexyl isocyanate, phenyl isocyanate, tolyl isocyanate, p-chlorophenyl isocyanate, 2,4-dichlorophenyl isocyanate and trifluoromethyl-phenyl isocyanate. According to the present invention, these monoisocyanates may also be selectively carbodiimidized in mixtures with higher molecular weight polyisocyanate so that they may be used, for example, for liquefing 4,4'-diisocyanatodiphenylmethane without causing 4,4'-diisocyanatodiphenylmethane to take part in the reaction (in spite of its extrenely reactive isocyanate groups).

Carbodiimidization of these monoisocyanates and polyisocyanates or mixtures thereof is carried out in accordance with the present invention by bringing these isocyanates or solutions thereof in inert solvents, such as toluene, xylene, chlorobenzene, o-dichlorobenzene, decalin, dimethyl-formamide, dimethylacetamide, butyl acetate, carbon tetrachloride, trichloroethylene or tetramethyl urea into contact with preferably from about 0.2 to about 10%, by weight, and most preferably from about 1 to about 4%, by weight, (based on the isocyanate) of the catalyst-laden matrix at temperatures of from about 50° to about 200° C., preferably from about 130° to about 185° C. If desired, the reaction can be conducted under pressure. The reaction is most simply carried out by introducing the catalyst into the liquid or dissolved isocyanates with stirring and removing it by decanting or filtration when the desired degree of carbodiimidization has been reached. The degree of conversion may easily be followed by measuring the volume of $CO_2$ formed during the carbodiimidation reaction. The catalysts according to the invention may generally be used from 5 to 10 times without loss of activity. Carbodiimidization may, of course, be carried out continuously in a column provided suitable arrangements are made for unrestricted escape of the $CO_2$ evolved in the reaction.

From extensive analyticl investigations of the chemical changes in the catalyst molecule during the carbodiimidization reaction it may be concluded that the phosphine oxides fixed to the matrix by ionic bonds, as well as their thio analogues, are converted into phosphine imine derivatives in a first reaction step, whereupon a 4-membered ring is formed as an intermediate stage by the addition of a further isocyanate molecule, and this ring is finally decomposed into the carbodimide and at the same time the phosphine oxide group is restored. The reaction scheme is exemplified in FIG. 1. In FIG. 1, R and R', which may be the same or different, each represent radicals which may be obtained by the removal of an isocyanate group from an organic mono- or poly-isocyanate.

It is of particular technical interest that, as mentioned above, 4,4'-diisocyanatodiphenylmethane, its isomers and its higher molecular weight multi-nuclear homologues of the type which may be prepared by anilineformaldehyde condensation followed by phosgenation may, under suitable reaction conditions, (particle size and porosity of the catalyst, temperature and solvent, if used) act as a virtually inert "solvent" for the carbodiimidization of low molecular weight mono- and poly-isocyanates because, for steric reasons, they are incapable of diffusing to the active points of the catalyst matrix. The same applies to other aromatic polyisocyanates of higher molecular weight such as substituted diphenylmethane diisocyanates, diisocyanatodiphenyl ethers, the hydrogenation products of diphenylmethane diisocyanates, 1-isocyanato-3,3,5-trimethyl-5-isocyanatomethyl cyclohexane and the like. The catalysts according to the present invention may be adjusted to be so selective in their action that even very small quantities of isocyanates, such as phenyl isocyanate, hexamethylene diisocyanate, tetramethylene diisocyanate, lysine methy ester isocyanate, ω-chlorohexyl isocyanate or tolylene diisocyanates present in mixtures with such polyisocyanates may be selectively carbodiimidized on the catalyst matrix.

Figure 2:
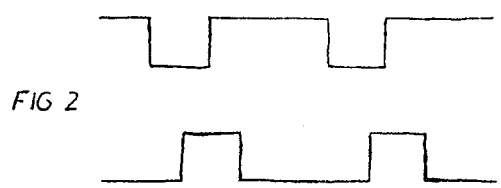
FIG. 2 is a representation of the structure of the catalyst of the instant invention.

The selectivity of the catalysts according to the present invention in carbodiimide formation is apparently similar to the function of enzymes in biological reactions. This is evidently due to the fact that the ability of mono- or poly-isocyanates to diffuse to the "active centres" or fit into the cavity of the matrix with active centres "A" as indicated in accompanying FIG. 2 (so that their isocyanate groups may reach the active center) is limited by their molecular size, depending on the size and numbers of the pores and degree of cross-linking of the high molecular weight matrix.

The diisocyanato-carbodiimides and triisocyanatouretone imines formed in the first stage of the carbodiimidization reaction by addition of another diisocyanate molecule to the diisocyanate-carbodiimide also have great difficulty in diffusing to the active centers of the catalyst matrix on account of their molecular size. It is therefore possible to achieve high degrees of carbodiimidization and yet obtain very low viscosity end products.

In this connection, it is revelant to point out again the technically interesting possibility of selectively converting small quantities of comparatively low molecular weight monoisocyanates or diisocyanates (preferably tolylene diisocyanate) present in polyisocyanates which are crystalline at room temperature (for example, diisocyanatodiphenylmethane or naphthylene diisocyanate) into diisocyanates which contain carbodiimide groups and which are then capable of adding another molecule of polyisocyanate to themselves to form uretone imine structures. Even relatively small proportions (from 3 to 12%, by weight, preferably from 4 to 8%, by weight) of these carbodiimide polyisocyanates or uretone imine polyisocyanates are sufficient to liquefy the polyisocyanate which is crystalline in the pure state.

In spite of the high functionality of the polyisocyanates in the so-called "modified" polyisocyanates (preferably those based on tolylene diisocyanate) which contain polyisocyanates modified with isocyanurate and/or allophanate and/or biuret and/or urethane groups, the selectivity of the catalysts according to the invention enables more than 20%, by weight, of so-called "monomeric diisocyanates" present in such mixtures to be converted into diisocyanate-carbodiimides or triisocyanato uretone imines without the formation of crosslinked products. This is a particularly surprising result in view of the fact that so-called "homogenous catalysis" with the aid of the conventional phospholine oxides would immediately result in cross-linking of the highly functional modified polyisocyanates.

As explained above, the selectivity of the high molecular weight used according to the present invention depends primarily on the porosity and particle size of the matrix, which may be varied within wide limits in conventional manner by suitable choice of the starting components (for example, in the case of polystyrenes which contain ionic groups, the proportion of styrene to divinyl benzene can be varied). In addition, the selectivity of the catalyst may be varied by the addition of a suitable solvent in which the matrix swells (for example xylene in the case of a polystyrene matrix). The activity of the catalyst may, of course, also be increased by raising the temperature. A catalyst which is highly selective towards isocyanates then becomes active towards isocyanates of increasingly larger molecular dimensions as the temperature increases (see Example 23). The selectivity of a given matrix laden with carbodiimidization catalyst may easily be determined by one skilled in the art on the basis of a simple test series in which the catalyst matrix is brought into contact with various monoisocyanates and polyisocyanates at different temperatures. Whether and how rapidly the carbodiimization reaction proceeds may be ascertained most simply by measuring the carbon dioxide evolved during the reaction.

It is, of course, not absolutely necessary according to the present invention to use high molecular weight catalysts which are selective in their action since the carbodiimidized (or only partially carbodiimidized) mono- and/or poly-isocyanates prepared according to the invention may easily be subsequently mixed with other polyisocyanates. This is another method of preparing mixtures which are stable in storage of high molecular weight and/or low molecular weight polyisocyanates with high molecular weight and/or low molecular weight carbodiimides and uretone imines which may contain isocyanate groups.

Since in the process according to the present invention the carbodiimization catalysts, in contrast to the catalysts previously known, may be completely removed, it is possible to prepare mixtures with any carbodiimide group content. However, according to the invention, it is preferred to prepare mixtures which contain from about 3 to about 70%, by weight, preferably from about 10 to about 60%, by weight, of carbodiimides or polycarbodiimides or uretone imines. As is well known in the art, uretone imines are addition compounds of a carbodiimide and an isocyanate. The following polyisocyanate/carbodiimide mixtures are particularly important technically:

(a) Mixtures of 100 parts by weight of 4,4'-diisocyanatodiphenylmethane and/or 1,5-naphthylene diisocyanate with from 5 to 30 parts by weight of an equilibrium mixture of the diisocyanatocarbodiimides of tolylene diisocyanate and the corresponding triisocyanato uretone imines.

(b) Mixtures of 100 parts by weight of 4,4'-diisocyanatodiphenylmethane and/or 1,5-naphthylene diisocyanate with from 10 to 30 parts by weight of an equilibrium mixture of carbodiimides of phenyl isocyanate, hexamethylene diisocyanate, tetramethylene diisocyanate, cyclohexyl isocyanate or tolyl isocyanate and the uretone imines thereof.

(c) Mixtures of 100 parts by weight of tolylene diisocyanate with from 5 to 30 parts by weight of an equilibrium mixture of carbodiimidized phenyl isocyanate or tolyl isocyanate and the uretone imines thereof.

(d) Mixtures of 100 parts by weight of modified tolylene diisocyanate containing from 10 to 40%, by weight, of biuret-, allophanate-, urethane- or isocyanurate- poly-isocyanates based on tolylene diisocyanate, with from 10 to 20 parts by weight of an equilibrium mixture of tolylene diisocyanate carbodiimide and the corresponding triisocyanato uretone imine.

(e) Mixtures of 100 parts by weight of biuret polyisocyanates of hexamethylene diisocyanate (preferably reaction products of 1 mol of water and from about 2 to 3 mol of hexamethylene diisocyanate) with from 10 to 30 parts by weight of the equilibrium mixture of the carbodiimide of hexamethylene diisocyanate and the corresponding uretone imine polyisocyanate.

(f) Mixtures of 100 parts by weight of $\alpha,\omega$-diisocyanato-prepolymers (obtained from 1 mol of $\alpha,\omega$-dihydro polyesters or polyethers of the type described in more detail below and from 1.4 to 2.5, preferably from 1.6 to 2 mol of tolylene diisocyanate, diisocyanatodiphenylmethane or hexamethylene diisocyanate) with from 5 to 30 parts by weight of the equilibrium mixture of the carbodiimides or carbodiimide diisocyanates and the corresponding uretone imine polyisocyanates of phenyl isocyanate, tolyl isocyanate, tetramethylene diisocyanate, hexamethylene diisocyanate or tolylene diisocyanate.

The carbodiimides prepared according to the present invention which carbodiimides may contain isocyanate groups, and their solutions in polyisocyanates which are free from carbodiimide groups are valuable starting materials for the diisocyanate polyaddition process and they may be used for the manufacture of various hard to elastic and, if desired, cellular plastics and for the production of lacquers, coatings, foils, and shaped products. Polyurethane produced in this way contain carbodiimide groups and uretone imine groups (=masked carbodiimide groups) which are firmly built into the polymer molecule and which act as age resistors against the hydrolysis of ester bonds, as well as reducing the flammability of the substances in which they are incorporated.

Production of the polyurethanes is carried out in conventional manner by reaction with high molecular weight and, if desired, low molecular weight, compounds which contain at least two hydrogen atoms which are reactive with isocyanate groups.

The compounds used for this purpose may contain amino groups, thiol groups or carboxyl groups, but they are preferably polyhydroxyl compounds. Particularly desirable compounds are those containing from two to eight hydroxyl groups and especially those having a molecular weight of from 400 to 10,000 and preferably from 800 to 6000, for example polyesters, polyethers, polythioethers, polyacetals, polycarbonates and polyester amides containing at least 2, generally from 2 to 8, but preferably from 2 to 4 hydroxyl groups, of the type which are generally known and used for the production of both homogenous and cellular polyurethanes.

Suitable polyesters with hydroxyl groups include, reaction products of polyhydric (preferably dihydric) alcohols with the optional addition of trihydric alcohols, and polybasic (preferably dibasic) carboxylic acids. Instead of free polycarboxylic acids, the corresponding polycarboxylic acid anhydrides or esters of lower alcohols or mixtures thereof may be used for preparing the polyesters. The polycarboxylic acids may be aliphatic, cycloaliphatic, aromatic and/or heterocyclic and they may be substituted (for example with halogen atoms) and/or unsaturated. The following are examples: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahydrophthalic acid anhydride, glutaric acid anhydride, maleic acid, maleic acid anhydride, fumaric acid, dimeric and trimeric fatty acids, such as oleic acid optionally in admixture with monomeric fatty acids, dimethyl terephthalate and bis-glycol terephthalate. Suitable polyhydric alcohols include ethylene glycol, propylene-1,2- and -1,3-glycol, butylene-1,4- and 2,3-glycol, hexane-1,6-diol, octane-1,8-diol, neopentyl glycol, cyclohexane dimethanol (1,4-bis-hydroxymethyl cyclohexane), 2-methyl-propane-1,3-diol, glycerol, trimethylolpropane, hexane-1,2,6-triol, butane-1,2,4-triol, trimethylolethane, pentaerythritol, quinitol, mannitol and sorbitol, methyl glycoside, diethylene glycol, triethylene glycol, tetraethylene glycol, polyethylene glycols, dipropylene glycol, polypropylene glycols, dibutylene glycol and polybutylene glycols. The polyesters may contain a proportion of carboxyl end groups. Polyesters of lactones, e.g. $\epsilon$-caprolactone, or of hydroxycarboxylic acids, e.g. $\omega$-hydroxycaprioc acid, may also be used.

The polyethers containing at least two, and generally from two to eight preferably two or three hydroxyl groups which may be used according to the invention are of the known type which may be prepared, for example, by the polymerization of epoxides, such as ethylene oxide, propylene oxide, butylene oxide, tetrahydrofuran, styrene oxide or epichlorohydrin, either alone, for example in the presence of $BF_3$, or by chemical addition of these epoxides, either as mixtures or successively, to starting components which contain reactive hydrogen atoms, such as water, alcohols or amines, e.g. ethylene glycol propylene-1,3- or 1,2-glycol, trimethylolpropane, 4,4'-dihydroxydiphenyl propane, aniline, ammonia, ethanolamine or ethylene diamine. Sucrose polyethers of the type which have been described in German Auslegeschrift Nos. 1,176,358 and 1,064,938, may also be used according to the present invention. In many cases, it is preferred to use polyethers which contain predominant amounts of primary OH-groups (up to 90%, by weight, based on all the OH-groups present in the polyether). Polyethers which are modified with vinyl polymers, for example the compounds obtained by the polymerization of styrene and acrylonitrile in the presence of polyethers (U.S. Pat. Nos. 3,383,351; 3,304,273; 3,523,093 and 3,110,695 and German Pat. No. 1,152,536) and polybutadienes which contain OH-groups are also suitable.

Among the polythioethers suitable are the condensation products obtained by condensing thiodiglycol on its own and/or with other glycols, dicarboxylic acids, formadehyde, aminocarboxylic acids or amino alcohols. The products obtained are polythio mixed ethers, polythioether esters or polythioether ester amides, depending on the co-components.

The polyacetals used included the compounds which may be prepared from glycols, such as diethylene glycol, triethylene glycol, 4,4'-dioxethoxy-diphenyl-dimethylmethane and hexane diol, with formaldehyde. Polyacetals suitable for the purpose of the invention may also be prepared by the polymerization of cyclic acetals.

Suitable polycarbonates which contain hydroxyl groups are known and include, for example, the compounds obtained by the reaction of diols, such as propane-1,3-diol, butane-1,4-diol and/or hexane-1,6-diol, diethylene glycol, triethylene glycol or tetraethylene glycol, with diaryl carbonates (such as diphenyl carbonate) or phosgene.

Suitable polyester amides and polyamides include the predominantly linear condensates obtainable from polybasic saturated and unsaturated carboxlyic acids or their anhydrides and polyvalent saturated and unsaturated amino alcohols, diamines, polyamines and mixtures thereof.

Polyhydroxyl compounds which already contain urethane or urea groups and modified or unmodified natural polyls, such as castor oil, carbohydrates or starch, may also be used. Addition products of alkylene oxides and phenol-formaldehyde resins or of alkylene oxides and urea-formaldehyde resins may also be used according to the present invention.

Mixtures of the above-mentioned compounds which contain at least two hydrogen atoms capable of reacting with isocyanates and have a molecular weight of from 400 to 10,000 may, of course, also be used, for example mixtures of polyethers and polyesters.

Representatives of these compounds which may be used according to the invention have been described, for example, in High Polymers, Volume XVI, "Polyurethanes, Chemistry and Technology", by Saunders Frisch, Interscience Publishers, New York, London, Volume I, 1962, pages 32–42 and pages 44–54, and Volume II, 1964, pages 5–6 and 198–199; and in Kunststoff-Handbuch, Volume VII, Vieweg-Höchtlen, Carl-Hanser-Verlag, Munich 1966, pages 45–71.

The starting components used according to the present invention can also include compounds having a molecular weight of from 32 to 400 which contain at least two hydrogen atoms capable of reacting with isocyanates. These compounds include compounds containing hydroxyl groups and/or amino groups and/or thiol groups and/or carboxyl groups. Preferable compounds of this type are those which contain hydroxyl groups and/or amino groups. These compounds serve as chain-lengthening agents or cross-linking agents. They generally contain from 2 to 8 hydrogen atoms which are reactive with isocyanates and preferably 2 or 3 such hydrogen atoms. The following are examples of such compounds: ethylene glycol, propylene-1,2- and -1,3-glycol, butylene-1,4- and -2,3-glycol, pentane-1,5-diol, hexane-1,6-diol, octane-1,8-diol, neopentyl glycol, 1,4-bishydroxymethyl-cyclohexane, 2-methyl-propane-1,3-diol, glycerol, trimethylolpropane, hexane-1,2,6-triol, trimethylolethane, pentaerythritol, quinitol, mannitol and sorbitol, diethylene glycol, triethylene glycol, tetraethylene glycol, polyethylene glycols having a molecular weight of up to 400, dipropylene glycol, polypropylene glycols having a molecular weight of up to 400, dibutylene glycol, polybutene glycols having a molecular weight of up to 400, 4,4'-dihydroxy-diphenylpropane, dihydroxymethyl hydroquinone, ethanolamine, diethanolamine, triethanolamine, 3-aminopropanol, ethylene diamine, 1,3-diaminopropane, 1-mercapto-3-aminopropane, 4-hydroxyphthalic acid or 4-aminophthalic acid, succinic acid, adipic acid, hydrazine, N,N'-dimethyl hydrazine and 4,4'-diaminodiphenylmethane. Mixtures of various compounds having a molecular weight of from 32 to 400 which contain at least two hydrogen atoms capable of reacting with isocyanates may also be used.

According to the invention, water and/or readily volatile organic substances can be used as blowing agents for the production of foams. Suitable organic blowing agents include, acetone; ethyl acetate; halogenated alkanes, such as methylene chloride, chloroform, ethylidene chloride, vinylidene chloride, nono-fluoro-trichloromethane, chlorodifluoromethane, or dichlorodifluoromethane; butane, hexane, heptane and diethyl ether. Compounds which decompose at temperatures above room temperature with the liberation of gases (such as nitrogen) may also act as blowing agents. These compounds include azo compounds, such as azoisobutyric acid nitrile. Other examples of blowing agents and details concerning the use of blowing agents may be found in Kunststoff-Handbuch, Volume VII, published by Vieweg and Höchtlen, Carl-Hanser-Verlag, Munich 1966, pages 108 and 109, 453 to 455 and 507 to 510.

According to the invention, known catalysts are frequently also added, for example tertiary amines, such as triethylamine, tributylamine, N-methyl morpholine, N-ethyl morpholine, N-cocomorpholine, N,N,N',N'-tetramethyl-ethylene diamine, 1,4-diaza-bicyclo-(2,2,2)-octane, N-methyl-N'-dimethylaminoethyl-piperazine, N,N-dimethyl benzylamine, bis-(N,N-diethylaminoethyl)-adipate, N,N-diethyl benzylamine, pentamethyl diethylene triamine, N,N-dimethyl cyclohexylamine, N,N,N',N'-tetramethyl-butane-1,3-diamine, N,N-dimethyl-β-phenyl ethylamine, 1,2-dimethyl imidazole and 2-imidazole. Suitable catalysts also include the known Mannich bases which may be obtained from secondary amines, such as diemthylamine, and aldehydes, preferably formaldehyde, or ketones, such as acetone methyl ethyl ketone or cyclohexanone, and phenols, such as phenol, nonyl phenol or bisphenol.

Tertiary amines containing hydrogen atoms which are reactive with isocyanate groups may also be used as catalysts. Examples include triethanolamine, triisopropanolamine, N-methyldiethanolamine, N-ethyl-diethanolamine, N,N-dimethyl-ethanolamine and their reaction products with alkylene oxides, such as propylene oxide and/or ethylene oxide.

Silaamines containing carbon-silicon bonds which have been described, for example, in U.S. Pat. No. 3,620,984 may also be used as catalysts. Examples include 2,2,4-trimethyl-2-silamorpholine and 1,3-diethylaminomethyl-tetramethyl-disiloxane.

The catalysts which may be used also include basic nitrogen compounds, such as tetralkyl ammonium hydroxides, alkali metal hydroxides, such as sodium hydroxide, alkali metal phenolates, such as sodium phenolate, and alkali metal alcoholates, such as sodium methylate. Hexahydrotriazines may also be used as catalysts.

According to the present invention, organic metal compounds may also be used as catalysts, particularly organic tin compounds.

The organic tin compounds used as catalysts are preferably tin (II) salts of carboxylic acids, such as tin(II)acetate, tin(II)octoate, tin(II)ethyl hexoate and tin(II)laurate and tin(IV)compounds, such as dibutyl tin oxide, dibutyl tin dichloride, dibutyl tin diacetate, dibutyl tin dilaurate, dibutyl tin maleate and dioctyl tin diacetate.

Any of the above-mentioned catalysts may, of course, be used as mixtures. Other examples of catalysts which may be used according to the present invention and details concerning the activity of the catalysts may be found in Kunststoff-Handbuch, Volume VII, published by Vieweg and Hochten, Carl-Hanser-Verlag, Munich 1966, pages 96 to 102.

The catalysts are generally used in a quantity of from about 0.001 to 10%, by weight, based on the quantity of compounds having a molecular weight of from 400 to 10,000 which contain at least two hydrogen atoms capable of reacting with isocyanate groups.

Surface-active additives, such as emulsifiers and foam stabilizers, may also be used according to the present invention. Suitable emulsifiers include the sodium salts of ricinoleic sulphonates or salts of fatty acids and amines, such as oleic acid diethylamine or stearic acid diethanolamine. Alkali metal ammonium salts of sulphonic acids, for example of dodecyl benzene sulphonic acid or dinaphthyl methane disulphonic acid or of fatty acids, such as ricinoleic acid, or of polymeric fatty acids may also be used as surface-active additives.

The foam stabilizers used are mainly polyether siloxanes, and are preferably those which are water-soluble. These compounds generally have a polydimethyl siloxane group attached to a copolymer of ethylene oxide and propylene oxide. Foam stabilizers of this type have been described in U.S. Pat. Nos. 2,834,748; 2,917,480 and 3,629,308.

Other additives which may also be used according to the invention include reaction retarders, e.g. compounds which are acid in reaction, such as hydrochloric acid or organic acid halides, cell regulators of the known type, such as paraffins or fatty alcohols or dimethyl polysiloxanes; pigments; dyes; known flame-retarding agents, such as tris-chloroethyl phosphate, tris-cresyl phosphate, and ammonium phosphate and polyphosphate; stabilizers against ageing and weathering; plasticizers; fungistatic and bacteriostatic substances; and fillers, such as barium sulphate, kieselguhr, carbon black or whiting.

Other examples of surface-active additives, foam stabilizers, cell regulators, reaction retarders, stabilizers, flame-retarding additives, plasticizers, dyes, fillers and fungistatic and bacteriostatic substances and the function and method of using these additives have been described in Kunststoff-Handbuch, Volume VII published by Vieweg and Hochtlen, Carl-Hanser-Verlag, Munich 1966, pages 103 to 113.

According to the present invention, the starting materials are reacted together by the known one-step process, prepolymer process or semi-prepolymer process, in many cases using mechanical devices such as those described, for example, in U.S. Pat. No. 2,764,565. Details concerning processing apparatus which may also be used according to the present invention may be found in Kunststoff-Handbuch, Volume VII, published by Vieweg and Hochtlen, Carl-Hanser-Verlag, Munich 1966, pages 121 to 205.

Production of foams according to the present invention is carried out by foaming inside molds. This process is carried out by introducing the reaction mixture into a mold made of a metal, such as aluminum, or a synthetic resin, such as an epoxide resin, in which the reaction mixture foams to form the molded product. This process of foaming inside a mold may either be carried out in such a way that the molded product has a cellular structure on its surface or it may be carried out to produce a product with a compact skin and a cellular core. According to the invention, one or other effect may be produced by either introducing just sufficient foamable reaction mixture into the mold to fill the mold with foam or introducing a larger quantity of reaction mixture than is necessary for filling the mold with foam. The latter method is known as overcharging. This procedure has been disclosed, for example in U.S. Pat. Nos. 3,178,490 and 3,182,104.

When foaming is carried out inside molds, so-called "external mold release agents" which are known, such as silicone oils, are frequently used. If desired, the external mold release agents may be used in conjunction with so-called "internal mold release agents", for example such as described in German Offenlegungsschrift Nos. 2,121,670 and 2,307,589.

Cold setting foams may also be produced according to the present invention (see, e.g. British Pat. No. 1,162,517, German Offenlegungsschrift No. 2,153,086).

If desired, the foams may, of course, also be produced by a process of block foaming or by the conventional double conveyor belt process.

The following Examples serve to explain the present invention. The quantities given represent parts by weight or percentages by weight unless otherwise indicated.

EXAMPLE 1

Preparation of 1-methyl-1-oxophospholane phosphonic acid dimethyl ester

A total of 117 g of an approximately 1:1 mixture of 1-methyl-1-oxophospholine-2 and 1-methyl-1-oxophospholine-3 is added dropwise in the course of 1 hour to 550 g of dimethyl phosphite in a 1 liter glass flask at a temperature of from 113° to 115° C. with vigorous stirring. At the same time, a suspension of 8 g of dibenzoyl peroxide in silicone oil is introduced gradually in the course of the reaction time. All the materials used have been freed from traces of oxygen by repeated evacuation and flushing with nitrogen.

After termination of the reaction, the dimethyl phosphite is distilled off under vacuum, followed by unreacted 1-methyl-1-oxophospholine (81 g) which consists of approximately equal parts of the two isomers. Distillation of the residue yields 28 g of an almost colorless oil ($bp_{0.5}$ mm: 185° to 190° C.) which solidifies in the receiver to a white crystalline paste which becomes liquid again at temperatures of from 40° to 55° C.

Analysis: $C_7H_{16}O_4P_2$—Calculated: 27.4% P, 37.2% C, 7.1% H; Observed: 28.0% P, 36.8% C, 7.0% H.

According to gas chromatographic analysis, 4 different isomers are obtained.

Acid saponification of this copound leads to the isomeric 1-methyl-1-oxophospholane-phosphonic acids which have the following idealized constitution:

(see Example 7)

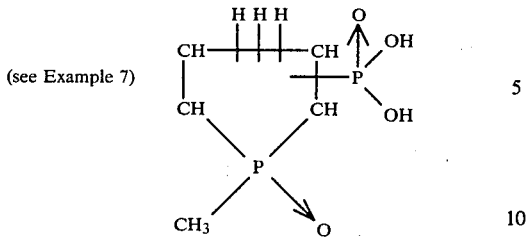

These isomers may be fixed to basic, insoluble matrices in large quanities (from 30 to 50%, by weight) in aqueous solution or in inert organic solvents. This reaction is accompanied by polyammonium salt formation or by neutralization on hydroxyl apatites.

EXAMPLE 2

Preparation of 1-methyl-1-oxophospholane phosphonic acid dimethyl ester 2900 g of 1-methyl-1-oxophospholine (mixture of isomers as in Example 1) and 200 g of tert.-butyl peroctoate dissolved in 750 ml of dimethyl phosphite are added dropwise to 5500 g of dimethyl phosphite at from 110° to 115° C. with stirring in the course of 4 hours. The reaction is carried out in a nitrogen atmosphere. After removal of excess dimethyl phosphite and unreacted phospholine oxide (170 g) by distillation, a residue of 5250 g of 1-methyl-1-oxophospholane phosphonic acid dimethyl ester (93% of the theoretical yield) which solidifies at from 50° to 60° C. is obtained.

Analysis: $C_7H_{16}O_4P_2$—Calculated: 27.4% P, 37.2% C, 7.1% H; Observed: 27.2% P, 37.0% C, 7.0% H.

EXAMPLE 3

Preparation of 1-methyl-1-oxophospholane phosphonicacid diethyl ester 1380 g of diethyl phosphite are heated to 160° C. under nitrogen. 348 g of 1-methyl-1-oxophospholine and 18 g of tert.-butyl peroxide are simultaneously added dropwise at this temperature in the course of 2 hours with vigorous stirring. Any unreacted diethyl phosphite is distilled off under vacuum. The residue consists of 755 g of a yellow liquid which according to elemental analysis and NMR has the composition of a 1-methyl-1-oxophospholanephosphonic acid diethyl ester. The substance may be distilled off at from 220° to 225° C./1 Torr with slight decomposition.

Analysis: $C_9H_{20}O_4P_2$—Calculated: 24.4% P, 42.5% C, 7.9% H; Observed: 24.2% P, 42.8% C, 7.8% H.

EXAMPLE 4

Preparation of 1-methyl-1-oxophospholanyl methyl phosphinic acid methyl ester 6 g of tert.-butyl peroctoate in 30 g of methane phosphonous acid methyl ester and 116 g of 1-methyl-1-oxophospholine are added dropwise to 282 g of oxygen-free methane phosphonous acid methyl ester at 120° C. with stirring. The reaction time is 90 minutes. Excess methane phosphonous acid methyl ester and a small quantity of 1-methyl-oxophospholine are distilled off. The residue, consisting of 205 g of 1-methyl-1-oxophospholanyl-methyl phosphinic acid methyl ester is purified by distillation under vacuum (bp$_1$ $_{mm}$: 210° to 220° C.) to yield 186 g of pure product which solidifies very slowly to stellate crystals which begin to reliquefy at 70° C. Acid saponification leads to isomeric 1-methyl-1-oxo-phospholanylmethyl phosphinic acids of the idealized constitution:

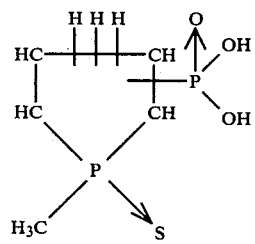

EXAMPLE 5

Preparation of 1-methyl-1-thiophospholane phosphonic acid dimethyl ester 132 g of 1-methyl-1-thiophospholine are added dropwise to 550 g of dimethyl phosphite in the course of 1 hour at a temperature of from 115° to 120° C. in a nitrogen atmosphere. 10 g of tert.-butyl peroctoate in 40 ml of dimethyl phosphite are introduced over the same period of time. Excess dimethyl phosphite and part of the unreacted 1-methyl-1-thiophospholine are recovered by distillation up to a sump temperature of 130° C. at 1 mm. Hg. The residue (148 g) consists of 1-methyl-1-thiophospholane phosphonic acid dimethyl ester contaminated with approximately 10% of 1-methyl-1-thio-phospholine. When this residue is dissolved in 500 ml of water and extracted with 40 ml of trichloroethylene, an aqueous solution which is free from 1-methyl-1-thio-phospholine is obtained. 118 g of 1-methyl-1-thiophos-pholane phosphonic acid dimethyl ester may be re-extracted from this solution with chloroform. Acid saponification of the extracted compound yields isomeric 1-methyl-1-thiophospholane phosphonic acids which have the idealized constitution:

EXAMPLE 6

Preparation of 1-methyl-1-oxophospholane thiophosphonic acid dimethyl ester 58 g of 1-methyl-1-oxophospholine and 3 g of tert.-butyl peroctoate in 5 ml of 1-methyl-1-oxophospholine are simultaneously added dropwise to 132 g of dimethyl thiophosphite with stirring in a nitrogen atmosphere. The reaction temperature is from 120° to 125° C. After removal of the dimethyl thiophosphite and a small quantity of 1-methyl-1-oxophospholine by distillation, the residue obtained consists of 121 g of 1-methyl-1-oxo-phospholane thiophosphonic acid dimethyl ester which solidifies in a crystalline form on cooling. The colorless crystals begin to reliquefy at 80° C. Acid saponification of this compound results in isomers of the following constitution:

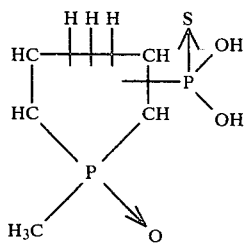

EXAMPLE 7

Preparation of 1-methyl-1-oxophospholane phosphonic acid 226 g of 1-methyl-1-oxophospholane phosphonic acid dimethyl ester are heated to boiling with 500 g of water and 300 g of 36% hydrochloric acid for 3 days. Methyl chloride and methanol distill off. The residue is evaporated under vacuum, taken up 6 times with 200 g of water and re-evaporated. No more chloride may then be detected in the residue which consists of pure 1-methyl-1-oxophospholane phosphonic acid. Equivalent weight observed: 98.2; calculated: 99.

Saponification of the compounds from Examples 3 to 6 may be carried out in analogous manner. Fixation of the free acids to the basic matrices can be carried out by the procedure employed in Examples 8 to 13.

EXAMPLE 8

This Example and the following Examples 9 to 13 describe procedures which are representative of the numerous possible methods of ionic fixation of the catalysts to insoluble basic matrices.

200 ml of a so-called "weak basic" anion exchanger based on a polystyrene containing —N—(CH$_3$)$_2$-groups, which has been regenerated with sodium hydroxide solution, (and which is produced according to Example 6 of U.S. Pat. No. 3,006,866, but contains only 5 percent by weight of divinyl benzene) are treated in a column with 30 g of 1-methyl-1-oxophospholane phosphonic acid in 300 ml of water. The exchanger resin has a macroporous structure and a total capacity of 1.9 val/l. When the resin has been laden with 1-methyl-1-oxophospholane phosphonic acid, it is washed with 3 l of water and dried in a vacuum at 90° C. The dried exchanger resin contains approximately 30% by weight of 1-methyl-1-oxophospholane phosphonic acid.

EXAMPLE 9

Example 8 is repeated with 300 ml of a macroporous, strongly basic anion exchanger based on a polystyrene which has a total capacity of 1.2 val/l and contains trimethyl ammonium groups (the exchanger is produced according to Example 2 of U.S. Pat. No. 3,006,866). A resin containing about 20% by weight of 1-methyl-1-oxophospholane phosphonic acid is obtained.

EXAMPLE 10

71 g of 1-methyl-1-oxophospholane phosphonic acid are added in the form of a 14% solution in water to 500 ml of a strongly basic, polystryene-based exchanger resin which has been regenerated with sodium hydroxide solution. The resin has a macroporous structure and a total capacity of 1.2 val/l and contains dimethyl-hydroxyethyl ammonium ions as anchoring groups in the solid phase (the exchanger is produced according to Example 5 of U.S. Pat. No. 3,066,866 utilizing the polystyrene of Example 2 of that patent). After a contact time of 30 minutes, the charged resin is washed three times, each time with 1 l of water, and then dried in a vacuum. About 30 g of 1-methyl-1-oxophospholane phosphonic acid are bound to 100 g of dried resin.

EXAMPLE 11

500 ml of a medium basic exchanger in the form of a gel based on a polycondensate of epichlorohydrin and triethylene tetramine containing trimethyl ammonium groups bound in the solid phase in addition to dimethylamine groups are regenerated with sodium hydroxide solution and washed with water until neutral. The exchanger, which has a total capacity of 2.2 val/l (and is produced according to U.S. Pat. No. 3,725,313) is brought into contact with 600 ml of an 18% aqueous 1-methyl-1-oxophospholane phosphonic acid solution which still contains 0.16 mol of hydrochloric acid. After a contact time of 2 hours, the aqueous phase is removed and the solid phase is washed 4 times with 1 l portions of water and then dried in a vacuum. The dry preparation contains 36% of 1-methyl-1-oxophospholane phosphonic acid.

EXAMPLE 12

The macroporous, strongly basic anion exchanger of Example 9 which contains trimethyl amonium ions as anchoring groups is charged with the following compounds instead of with 1-methyl-1-oxophospholane phosphonic acid in the same way as described in Example 9:

(a) 1-methyl-1-oxophospholane phosphinic acid
(b) 1-methyl-1-thiophospholane phosphonic acid
(c) 1-methyl-1-oxophospholane thiophosphonic acid.

The following quantities are fixed:

(a) 32 parts, by weight, to 68 parts, by weight, of matrix
(b) 29 parts, by weight, to 71 parts, by weight, of matrix
(c) 27 parts, by weight, to 73 parts, by weight, of matrix.

EXAMPLE 13

By employing the procedure described in Example 8, the compound of the following formula:

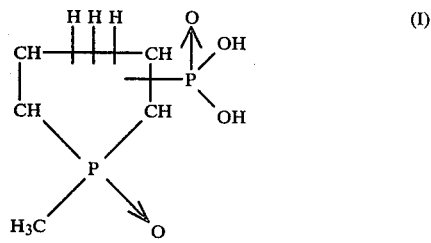  (I)

may be fixed in the quantities, by weight, indicated below by way of quaternary ammonium salt groups to various basic matrices of differing porosity which act as anion exchangers:

(A) About 36 parts, by weight, of compound (I) are fixed to 64 parts, by weight, of a medium basic anion exchanger in the form of a gel based on a phenolformaldehyde resin which is only slightly porous and contains the following anchoring group:

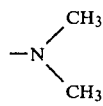

The resin was prepared as follows: 1 mol of phenol and 3 mol of formaldehyde were first condensed for 4 hours in 0.5 l of water at pH=1 and at a temperature of 80° C., using hydrochloric acid as catalyst. The unsoluble precipitate was filtered off and dried. The condensation product was then chloromethylated under reflux with 1.5 mol of paraformaldehyde and gaseous hydrochloric acid for 4 hours in 0.5 l of carbon tetrachloride in conventional manner.

In a third stage, the product obtained from the second stage was dissolved in toluene and reacted with an excess of gaseous dimethylamine at 100° C. in an autoclave for 2 hours. The pulverulent material obtained was finally washed free from chloride with normal sodium hydroxide solution.

(B) About 30 parts, by weight, of compound (I) were fixed to 70 parts, by weight, of a medium basic, macroporous anion exchanger in the form of a gel based on a phenolformaldehyde-urea-formaldehyde polycondensate which contained N-CH$_3$-groups as anchoring groups. The polycondensate had been prepared by reacting 1 mol of phenol, 1 mol of:

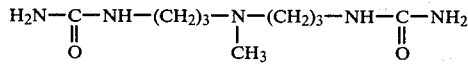

and 5 mol of formaldehyde for 2 hours in 800 ml of water at 80° C. and pH=1 with the aid of hydrochloric acid as catalyst and then washing the reaction product free from chloride with normal sodium hydroxide solution.

(C) About 30 parts, by weight, of compound (I) are fixed to 70 parts, by weight, of a strongly basic macroporous anion exchanger based on polystyrene containing:

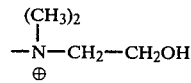

as anchoring groups (the exchanger of Example 10).

(D) Approximately 23 parts, by weight, of compound (I) are fixed to 77 parts, by weight, of a very strongly basic, not macroporous anion exchanger based on polystyrene cntaining

groups as anchoring groups (produced according to Example 2 of U.S. Pat. No. 3,006,866, but without using the white spirit and containing only 5% divinyl benzene).

(E) Approximately 32 parts, by weight, of compound (I) are fixed to 68 parts, by weight, of a very strongly basic, not macroporous anion exchanger based on polystyrene containing

groups as anchoring groups.

Matrices based on polystyrene may be produced with differing porosities by copolymerizing styrene with from 2 to 6% by weight, of divinyl benzene by the method of bead polymerization (Houben-Weyl, Volume XIV/1 (1961), Makromolekulare Stoffe, pages 146, 406, 425, 840, 1122 and 1129). The bead polymers obtained are subsequently chloromethylated (Houben-Weyl, Volume XIV/2, Makromolekulare Stoffe (1963), page 667) to convert them into cross-linked polystyrene beads containing —CH$_2$Cl-groups. Reaction of this polystyrene containing reactive chloromethyl groups with: (CH$_3$)$_2$N—CH$_2$CH$_2$OH results in carriers like matrix (C) while reaction with trimethylamine results in carriers like matrices (D) and (E). See also U.S. Pat. No. 3.006,866.

(F) Approximately 30 parts, by weight, of compound (I) are fixed to 70 parts, by weight, of a very strongly basic anion exchanger based on polystyrene which has been prepared according to Example 2 of U.S. Pat. No. 3,006,866 (but containing only 5% by weight, of divinylbenzene) which has a macroporous structure and contains

anchoring groups.

Matrix (F) has a pore volume of about 55%, a pore surface of from 40 to 50 m$^2$ per gram of dry substance and an average pore diameter of from 200 to 400 Ångström units. The particle size is from 0.3 to 1.5 mm. The capacity of matrix (F) to swell in aliphatic polyisocyanates is from about 30 to 40 vol. %, measured by the increase in volume of the beads, and its capacity to swell in aromatic isocyanates, such as phenyl isocyanate or tolylene-2,4-diisocyanate, is from approximately 90 to 130 vol. %. The matrix contains 2×10$^{18}$ basic groups per mg of dry substance.

(G) About 20 parts, by weight, of compound (I) are fixed to 80 parts, by weight, of a polyethylene imine granulate which has been cross-linked with Cl—CH$_2$—CH$_2$—CH$_2$CH$_2$—Cl.

The granulate had been prepared in the following manner: 200 parts, by weight, of polyethylene imine (average molecular weight about 6000) were dissolved in 600 parts, by weight, of water. 80 parts, by weight, of dichlorobutane were added and the reaction was carried out in heterogenous phase by heating the composition for 2 hours at 130° C. in an autoclave. The rubber-like product thus obtained was filtered off and carefully washed with normal sodium hydroxide solution and water.

(H) Approximately 5 parts, by weight, of (I) are fixed to 95 parts, by weight, of a natural, inorganic apatite powder containing hydroxyl groups when the powder is exposed to the action of (I) for 30 hours.

(I) Approximately 15 parts, by weight, of compound (I) are fixed to approximately 80 parts, by weight, of an insoluble, cross-linked, basic polyurea powder which has been prepared by reacting 1 mol of a biuret triisocyanate of the idealized structure:

$$\text{OCN}-(\text{CH}_2)_6-\text{N}-\overset{\overset{\text{O}}{\|}}{\text{C}}-\text{NH}-(\text{CH}_2)_6-\text{NCO}$$
$$\underset{\text{NH}-(\text{CH}_2)_6-\text{NCO}}{\overset{\text{C}=\text{O}}{|}}$$

with 1 mol of:

$$\text{H}_2\text{N}-(\text{CH}_2)_3-\underset{\text{CH}_3}{\overset{|}{\text{N}}}-(\text{CH}_2)_3-\text{NH}_2$$

in 600 ml of xylene as dispersing agent at 30° C.

(J) Approximately 25 parts, by weight of compound (I) are fixed to approximately 75 parts, by weight, of a basic polyurethane powder which has been prepared from 1 mol of hexamethylene diisocyanate and 1 mol of:

$$\text{HOCH}_2\text{CH}_2-\underset{\text{CH}_3}{\overset{|}{\text{N}}}-\text{CH}_2-\text{CH}_2-\text{OH}$$

by heating the two starting components for 2 hours at 60° C. in 600 ml of xylene as dispersing agent.

(K) Approximately 15 parts, by weight, of compound (I) are fixed to approximately 84 parts, by weight, of a cross-linked basic polyepoxide granulate. The granulate had been prepared by heating a mixture comprising 1 mol of:

$$\text{CH}_2\!\!-\!\!\text{CH}\!-\!\text{CH}_2\!-\!\!\!\left\langle\!\!\!\begin{array}{c}\phantom{x}\end{array}\!\!\!\right\rangle\!\!-\!\!\underset{\text{CH}_3}{\overset{\overset{\text{CH}_3}{|}}{\text{C}}}\!-\!\!\!\left\langle\!\!\!\begin{array}{c}\phantom{x}\end{array}\!\!\!\right\rangle\!\!-\!\text{CH}\!-\!\text{CH}_2$$
(epoxide rings on terminal CH₂—CH groups)

and 1 mol of:

$$\text{H}_2\text{N}-(\text{CH}_2)_3-\underset{\text{CH}_3}{\overset{|}{\text{N}}}-(\text{CH}_2)_3-\text{NH}_2$$

for 4 hours at 90° C. in 800 ml of xylene as dispersing agent. The coarse precipitate thus obtained was filtered off and dried.

(L) Approximately 12 parts, by weight, of compound (I) are fixed to approximately 88 parts, by weight, of a basic, granular copolymer which has been prepared by radical-initiated emulsion copolymerization by reacting 1 mol of styrene and 0.5 mol of:

$$\text{CH}_2=\underset{\text{CH}_3}{\overset{|}{\text{C}}}-\overset{\overset{\text{O}}{\|}}{\text{C}}-\text{NH}-\text{CH}_2-\text{CH}_2-\text{CH}_2$$
$$\phantom{xxxxxxxxxxxxxxxxxxxxxxxxxxxxx}\diagdown$$
$$\phantom{xxxxxxxxxxxxxxxxxxxxxxxxxxxxxxxx}\text{N}-\text{CH}_3$$
$$\phantom{xxxxxxxxxxxxxxxxxxxxxxxxxxxxx}\diagup$$
$$\text{CH}_2=\underset{\text{CH}_3}{\overset{|}{\text{C}}}-\overset{\overset{\text{O}}{\|}}{\text{C}}-\text{NH}-\text{CH}_2-\text{CH}_2-\text{CH}_2$$

for 4 hours at 65° C. in 1 l of water, using benzoyl peroxide as starter and 4 g of a high molecular weight polyethylene oxide as emulsifier.

(M) Approximately 15 parts, by weight, of compound (I) are fixed to approximately 85 parts, by weight, of a polymethylene urea powder containing basic groups, which was prepared from 1 mol of $$\text{H}_2\text{N}-\overset{\overset{\text{O}}{\|}}{\text{C}}-\text{NH}_2,$$

2 mol of formaldehyde and 1 mol of:

$$\text{H}_2\text{N}-\overset{\overset{\text{O}}{\|}}{\text{C}}-\text{NH}-(\text{CH}_2)_3-\underset{\text{CH}_3}{\overset{|}{\text{N}}}-(\text{CH}_2)_3-\text{NH}-\overset{\overset{\text{O}}{\|}}{\text{C}}-\text{NH}_2$$

by condensation (in 0.6 liters of hydrochloric acid at pH=1 and room temperature) and subsequently washed free from chloride by vigorous treatment with normal NaOH.

(N) 17 parts, by weight, of compound (I) are fixed to 83 parts, by weight, of a urethane modified polyvinyl alcohol resin containing basic groups. The resin was prepared by reacting, for 4 hours at 50° C., 88 g of polyvinyl alcohol (average molecular weight about 20 000) and 1 mol of:

$$\underset{\text{H}_3\text{C}}{\overset{\text{H}_3\text{C}}{\diagdown}}\!\!\text{N}-\text{CH}_2-\text{CH}_2-\text{O}-\overset{\overset{\text{O}}{\|}}{\text{C}}-\text{NH}-(\text{CH}_2)_6-\text{NCO}$$

in 500 ml of dimethylformamide as dispersing agent, using 0.4 g of tin(II)octoate as catalyst.

By addition of water, the resin was precipitated from the dimethylformamide, followed by filtering off and drying.

(O) 20 parts, by weight, of compound (I) are fixed to 80 parts, by weight, of a pulverulent, basic polyamide which was prepared from 1 mol of adipic acid, 1 mol of hexamethylene diamine and 1 mol:

$$\text{H}_2\text{N}-(\text{CH}_2)_3-\underset{\text{CH}_3}{\overset{|}{\text{N}}}-(\text{CH}_2)_3-\text{NH}_2$$

by a 6 hours' solvent-free condensation under nitrogen at 220° C.

(P) 35 parts, by weight, of compound (I) are fixed to 65 parts, by weight, of a polyguanidine in the form of a coarse powder. The polyguanidine was prepared from a high molecular weight, cross-linked polycarbodiimide of 4,4'-diisocyanatodiphenylmethane (obtained by polymerizing 4,4'-diisocyanatodiphenylmethane in the conventional manner in the presence of catalytical amounts of phospholine oxide, followed by boiling the cured, cross-linked resin with aqueous alcohol to remove all traces of the catalysts) in an autoclave by chemical addition of approximately equivalent quantities of dimethylamine (a), methylamine (b) or ethylamine (c) in xylene as dispersing agent at 160° C. and 10 excess atmospheres and which in the case of (a) contains the following basic groups in the polymer matrix:

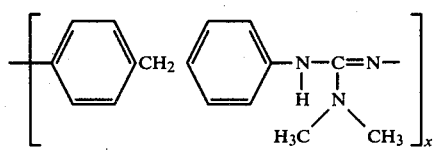

x = approx. 3 to 12 as anchoring group for phospholinic, phosphonic, phosphinic or thiophosphonic acids.

(Q) 19 parts by weight of compound (I) are fixed to 81 parts by weight of an insoluble matrix which has been cross-linked through polysiloxane groups. The matrix was prepared by the reaction of 4 mol of tolylene-2,4-diisocyanate, 1 mol of:

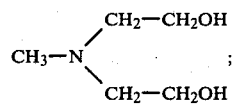

and 4 mol of $C_6H_{11}$—NH—$CH_2$-Si(—$OC_2H_5$)$_3$ in 600 ml of xylene as dispersing agent at 70° C. By distilling off the xylene from the clear solution thus obtained by water vapor distillation, the linear polyurethane was subsequently cross-linked three-dimensionally across siloxane groups.

(R) (1) 25 parts by weight of compound (I) are fixed to 78 parts by weight of an insoluble matrix which has a high siloxane group content and which was prepared by adding a mixture of comprising 1 mol of:

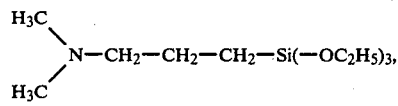

2 mol of:

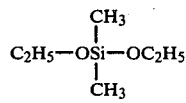

and 2 mol of:

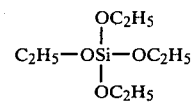

dropwise in the course of ½ hour to a mixture of 178 l methanol and ½ l of water at 50° C. followed by stirring the reaction mixture for 4 hours at 50° C., filtering off the precipitate and drying.

(2) 40 parts by weight of compound (I) are fixed to 78 parts by weight of an analogous insoluble matrix with a high siloxane group content which has been prepared by hydrolysis of 1 mol of:

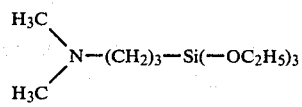

in an analogous manner as described above.

(3) 30 parts by weight of compound (I) are fixed to 78 parts by weight of an analogous matrix prepared by cohydrolysis of 1 mol of $(CH_3)_2N$—$CH_2$—$Si(OC_2H_5)_3$ and 4 mol of $Si(—OC_2H_5)_4$ as described above.

EXAMPLE 14

The insoluble catalysts (A) to (R) described in Example 13 are used for the heterogeneous catalysis of carbodiimidization of 2088 parts by weight, (12 mol) of an isomeric mixture, which is liquid at room temperature, of 80% by weight of tolylene-2,4-diisocyanate and 20% by weight of tolylene-2,6-diisocyanate. The insoluble catalyst is used in each case in the quantity by weight indicated in the following Table 2.

The catalyst is kept in suspension in the polyisocyante by vigorous stirring at a temperature of from 148° to 151° C. Carbodiimidization sets in very rapidly and its velocity is measured with a $CO_2$ gas meter. In all 21 Examples of the Table, carbodiimidization is continued to the same degree of conversion by stopping the reaction by simple removal of the catalyst by filtration when 76 l of $CO_2$ have been evolved. The reaction times given in the Table are a measure of the differences in the velocity of carbodiimidization which depends on the rate of diffusion of the diisocyanate to the active center of the matrix and hence on the porosity of the matrix.

TABLE 2

| Catalyst | Parts by weight of catalyst | Quantity of $CO_2$ evolved in liters | —N=C=N— equivalents | Reaction time in hours | % NCO of the solution | Viscosity in cP/20° C |
|---|---|---|---|---|---|---|
| A (polycondensate matrix) | 28 | 76 | 3.4 | 8 | 34.8 | 48 |
| B (polycondensate matrix) | 30 | 76 | 3.4 | 9 | 35.1 | 55 |
| C (polymer matrix) | 24 | 76 | 3.4 | 4 | 34.8 | 46 |
| D (polymer matrix) | 24 | 76 | 3.4 | 9 | 34.6 | 51 |
| E (polymer matrix) | 24 | 76 | 3.4 | 10 | 35 | 65 |
| F (polymer matrix) | 24 | 76 | 3.4 | 5.5 | 34.9 | 46 |
| G (polycondensate matrix) | 30 | 76 | 3.4 | 11 | 35.1 | 45 |
| H (Apatite) | 60 | 76 | 3.4 | 24 | 35.8 | 42 |
| I (poly- | | | | | | |

TABLE 2-continued

| Catalyst | Parts by weight of catalyst | Quantity of $CO_2$ evolved in liters | —N=C=N— equivalents | Reaction time in hours | % NCO of the solution | Viscosity in cP/20° C |
|---|---|---|---|---|---|---|
| addition matrix) | 30 | 76 | 3.4 | 9 | 35.1 | 64 |
| J (polyaddition matrix) | 32 | 76 | 3.4 | 10 | 34.7 | 49 |
| K (polyaddition matrix) | 40 | 76 | 3.4 | 8 | 35.5 | 42 |
| L (polymer matrix) | 45 | 76 | 3.4 | 7 | 34.4 | 70 |
| M (polycondensate matrix) | 40 | 76 | 3.4 | 7 | 35.2 | 54 |
| N (polycondensate matrix) | 30 | 76 | 3.4 | 8 | 34.2 | 74 |
| O (polycondensate matrix) | 35 | 76 | 3.4 | 8.5 | 35.2 | 42 |
| P (polyaddition matrix) | 28 | 76 | 3.4 | 9.8 | 34.7 | 55 |
| Q (polyaddition polycondensation matrix containing Si) | 32 | 76 | 3.4 | 12 | 35.4 | 42 |
| $R_1$ (polycondensate matrix containing silicon) | 15 | 76 | 3.4 | 14 | 34.9 | 48 |
| $R_2$ | 12 | 76 | 3.4 | 8 | 35.8 | 42 |
| $R_3$ | 14 | 76 | 3.4 | 9 | 36.1 | 39 |

Determination of the quantity of $CO_2$ evolved at 20° C. and of the isocyanate content and spectroscopic investigations indicate in all cases that approximately 53.5% of the tolylene diisocyanate initially react to form the diisocyanato-carbodiimide of the formula:

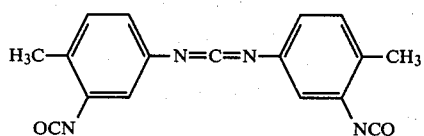

(and the corresponding 2,6-isomers, respectively) of which at least 65 to 70% are then converted into the uretone imine triisocyanate of e.g. the following constitution:

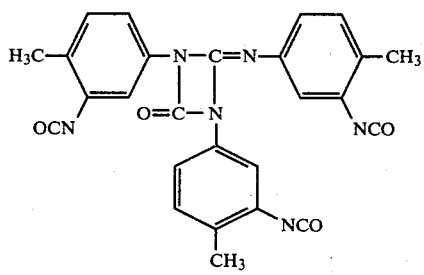

ps (and the corresponding 2,6-isomers, respectively) by the free tolylene diisocyanate still present. In all the 21 Examples, therefore, the solutions contain at least about 65 to 70% by weight of partially masked carbodiimide diisocyanates in tolylene diisocyanate.

The solutions of diisocyanato carbodiimides prepared in this way, which are in equilibrium with triisocyanato urethane imines, are all completely stable over a period of 6 months without developing any $CO_2$ pressure when stored in closed vessels.

EXAMPLE 14 A (Comparison Experiment)

If the method described in Example 14 is used for the formation of isocyanato carbodiimides and isocyanatopolycarbodiimides, but 4 parts by weight of isomeric phospholine oxides of the following formulae:

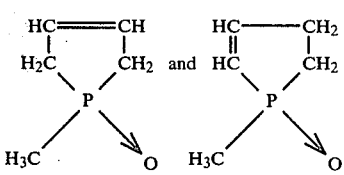

are used as catalyst for homogeneous catalysts, vigorous carbodiimide formation sets in at room temperature. However, the reaction cannot be stopped and therefore cannot be used for preparing stable solutions of carbodiimide diisocyanates and uretone imine triisocyanates in excess monomeric polyisocyanates. After only 2 hours, the solution has solidified to a brittle foam. If, for comparision from 1 to 5% by weight of $POCl_3$, zinc chloride dimethyl carbamic acid chloride, $PCl_5$, aluminum chloride, BF$_3$ or gaseous HCl are added to the solution as inhibitors after approx. 76 liters of CO$_2$ (determined at 20° C.) have been liberated, subsequent formation of carbodiimide is slowed down, but the isocyanate content of the solution continues to decrease with continuous evolution of CO$_2$ and increase in viscosity. These solutions cannot be transported in closed vessels and are considerable sources of danger due to the development of high CO$_2$ pressures which are likely to cause spontaneous explosion of the vessels.

EXAMPLE 15

The procedure is exactly the same as described in Example 13, but when catalyst (F) has been used once, it is used a second time and the evolution of CO$_2$ is plotted against time. Practically the same CO$_2$ curve is obtained as in the first experiment. Even after 5 times, the catalyst can be used again provided that after the catalyst has been filtered off, its porous structure is not destroyed by the action of atmospheric moisture and formation of polyurea.

EXAMPLE 16

This Example demonstrates the surprising selectivity of catalyst (F) described in Example 13 (matrix on a basis of polystyrene with strongly basic anchoring groups).

500 parts by weight of 4,4'-diisocyanatodiphenyl methane (2 mol) and 34.8 parts by weight (0.2 mol) of a mixture of 80 parts by weight of tolylene-2,4-diisocyanate and 20 parts by weight of tolylene-2,6-diisocyanate are heated to 165° C. for 35 minutes with 4 parts by weight of catalyst (F) the preparation of which was described in Example 13. Carbodiimidization of the tolylene diisocyanate proceeds selectively and a solution of about 7% by weight of the compound (or the 2,6-isomers, respectively)

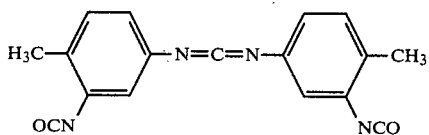

in 4,4'-diisocyanatodiphenylmethane is obtained. This solution has the remarkably low viscosity of only about 68 cP/20° C. and an isocyanate content of about 31.5% After equilibration with the diisocyanatodiphenylmethane more than 70% by weight of the diisocyanatocarbodiimide formed have been converted to a triisocyanatouretone imine of the idealized formula:

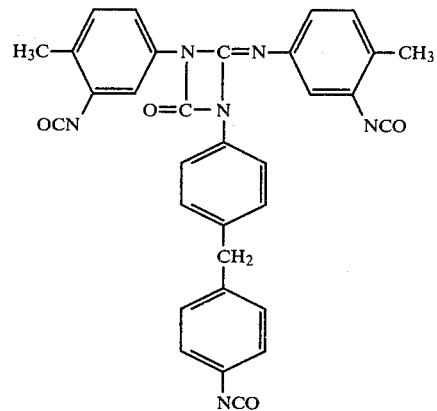

It is surprisingly found that even at concentrations of only about 7% by weight the diisocyanato-carbodiimide prepared according to the invention and its uretone imine triisocyanate are capable of liquefying 4,4'-diisocyanatodiphenylmehane whch is crystalline at room temperature.

EXAMPLE 17

As has been found in Example 16, carbodiimidization of tolylene diisocyanate with the aid of catalyst (F) from Example 13 proceeds strictly selectively at a temperature of 165° C. When the temperature is raised to 181° C., the pore size increases, partly due to thermal expansion and partly due to the increased degree of swelling, with the result that carbodiimidization no longer proceeds selectively and part of the diphenylmethane diisocyanate is also carbodiimidized. The carbodiimide polyisocyanates of 4,4'-diisocyanatodiphenylmethane are therefore obtained in addition to polycarbodiimide polyisocyanates of tolylene diisocyanate.

Thus, for example, when a mixture of 500 parts, by weight, (2 mol) of 4,4'-diisocyanatodiphenylmethane, 34.8 parts, by weight, (0.2 mol) of tolylene-2,4-diisocyanate and 4 parts, by weight, of catalyst (F) is reacted at from 178° to 181° C., 12.6 liters of CO$_2$ are liberated in the course of 4 hours. The reaction products consist of approximately 0.1 mol of:

$$\text{H}_3\text{C}-\bigcirc-\text{N}=\text{C}=\text{N}-\bigcirc-\text{CH}_3$$
$$\text{OCN} \qquad\qquad\qquad \text{NCO}$$

and the corresponding uretone imine triisocyanates and approximately 0.46 mol of diisocyanato-carbodiimides of the following constitution:

$$\text{OCN}-\bigcirc-\text{CH}_2-\bigcirc-\text{N}=\text{C}=\text{N}-\bigcirc-\text{CH}_2-\bigcirc-\text{NCO}$$

of which at least 70% react with 1.18 mol of the 4,4'-diisocyanatodiphenylmethane still present to produce uretone imine triisocyanates of the idealized construction:

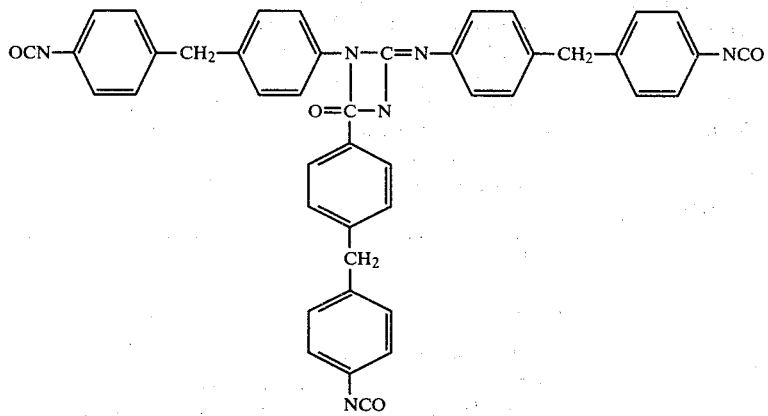

A polyisocyanate mixture which is liquid at room temperature and has an isocyanate content of 23.5% and a viscosity of 1182 cP/20° C. is obtained. It has excellent storage stability. It contains approximately 57%, by weight, of diisocyanato-carbodiimides and uretone imine triisocyanates of the idealized constitutions indicated above.

EXAMPLE 18

The procedure is exactly the same as in Example 16, but the 0.2 mol of tolylene diisocyanate is replaced by:
(a) 0.2 mol of phenyl isocyanate,
(b) 0.2 mol of 4-isocyanatotoluene,
(c) 0.2 mol of benzyl isocyanate,
(d) 0.2 mol of ω-chlorohexyl isocyanate and
(e) 0.2 mol of n-butyl isocyanate.

Selective carbodiimidization of the monoisocyanates described under (a) to (e) may be carried out as in Example 16 at a temperature of from 162° to 165° C., and again it is found that 4,4'-diisocyanatodiphenylmethane can be liquefied at room temperature.

The carbodiimides formed, in particular the carbodiimides R—N=C=N—R obtained from the aromatic monoisocyanate (a) and (b), wherein R represents phenyl, tolyl, benzyl, chlorohexyl or n-butyl, undergo an addition reaction with 4,4'-diisocyanatodiphenylmethane in accordance with the idealized reaction scheme indicated below to form the uretone imine monoisocyanate of the formula:

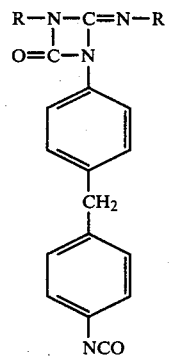

which is both a masked monocarbodiimide and a masked diisocyanate.

Stable solutions of polyisocyanate mixtures which contain carbodiimide groups or masked carbodiimide groups and have the following isocyanate contents and viscosities are obtained:

| (a) | 30.1 | % NCO | $\eta$ = 61 cP |
|-----|------|-------|----------------|
| (b) | 29.4 | % NCO | $\eta$ = 75 cP |
| (c) | 28.5 | % NCO | $\eta$ = 980 cP |
| (d) | 29.1 | % NCO | $\eta$ = 885 cP |
| (e) | 30.5 | % NCO | $\eta$ = 730 cP |

EXAMPLE 19

The selectivity of carbodiimidization may again be eliminated by simply increasing the temperature from about 160° to 165° C. to 180° to 185° C. so as to increase the pore size of the catalyst (F) due to thermal expansion and increased swelling in the diisocyanate mixture used. This is illustrated by the following method:

500 parts, by weight, of 4,4'-diisocyanatodiphenylmethane (2 mol) are mixed with 23.8 parts, by weight, of phenyl isocyanate (0.2 mol) and heated to 184° C. for 3 hours with 4 parts, by weight, of catalyst (F), the preparation of which was described in Example 13. 12.6 liters of $CO_2$ (measured at 20° C.) are evolved in the course of the reaction. Not only is phenyl isocyanate converted into diphenyl carbodiimide and the corresponding uretone imine monoisocyanates of 4,4'-diisocyanatodiphenylmethane, but a proportion of about 0.4 mol of 4,4'-diisocyanatodiphenylmethane is also converted into the corresponding diisocyanatocarbodiimide and its uretone imine triisocyanate.

The products of the process are obtained in the form of stable solutions in 4,4'-diisocyanatodiphenylmethane which will no longer crystallize at room temperature. Isocyanate content of the solution is 21.84%, while viscosity at 25° C. is 428 cP.

EXAMPLE 20

This Example illustrates the interesting finding that even commercial solutions containing about 30 parts, by weight, of (a) biuret polyisocyanates which according to gaschromatographic analysis are composed of about 35% by weight of triisocyanates; about 25% by weight of tetraisocyanates; about 19% by weight of pentaisocyanates, and about 18% by weight of highly functional biuret polyisocyanates which may be linked through uretdione groups, or (b) allophanate polyisocyanates or (c) isocyanurate polyisocyanates of tolylene-2,4-diisocyanate in about 70 parts, by weight, of monomeric tolylene diisocyanate may be selectively carbodiimidized by means of the catalysts according to the present invention. The higher molecular weight biuret polyisocyanates e.g. those of the constitution:

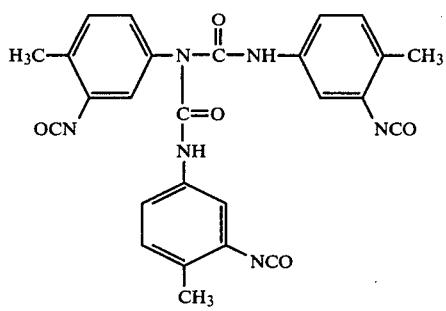

and their higher molecular weight homologues (a) or allophanate polyisocyanates which e.g. have the idealized constitution:

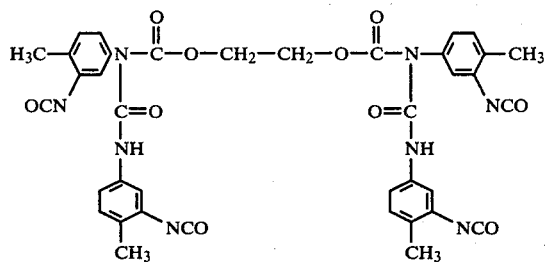

and their higher molecular weight homologues (b) or isocyanurate polyisocyanates (c) which have the idealized constitution:

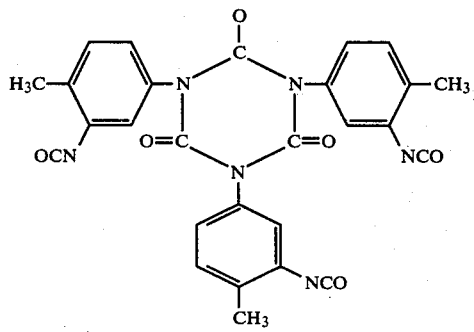

and higher molecular weight multi-nuclear polyisocyanurate polyisocyanates are obviously sterically hindered from reaching the active centers of the polymer matrix (F), and they are therefore not carbodiimidized. The only isocyanate which can easily diffuse to the active center of the matrix to enter into the carbodiimde reaction is tolylene diisocyanate, which is present as "solvent", and tolylene-2,4-diisocyanate, which has its isocyanate group in the para-position, can do so most rapdily.

The carbodiimidization reaction presumably proceeds in the following stages:

(1) primary formation of solid phosphine imine with liberation of $CO_2$ at the matrix;

(2) addition of another molecule of tolylene diisocyanate to the insoluble phosphine imine of the matrix;

(3) decomposition of the resulting 4-membered ring into carbodiimide, and (4) detachment of the carbodiimide from the matrix and simultaneous reformation of the phospholine oxide or phosphine matrix.

The approximately 30% solutions of the abovementioned polyisocyanates (a) to (c) in tolylene diisocyanate (ratio of isomers 2,4:2,6=80:20) have the following isocyanate contents and viscosities:

| (a) | 41.5 | % NCO | $\eta$ 20° C. = 212 cP |
|---|---|---|---|
| (b) | 39.8 | % NCO | $\eta$ 20° C. = 320 cP |
| (c) | 38.7 | % NCO | $\eta$ 20° C. = 290 cP |

The action of 24 parts, by weight, of catalyst (F) on 2000 parts, by weight, of these mixtures (a), (b) and (c)for 6 hours at 160° C. results in reaction products which are still completely free from gel. The reaction is accompanied by the liberation of about 37.6 liters of $CO_2$ (corresponding to the formation of from about 1.68 to 1.72 mold of:

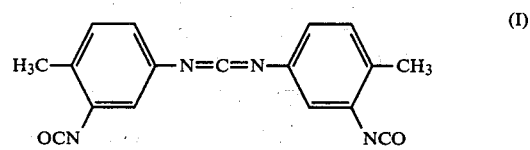

and of isocyanato uretone imine adducts of (I) and monomeric tolylene diisocyanate or of adducts of (I) and allophanate, biuret or isocyanurate polyisocyanates). The products of the process have the following isocyanate contents and viscosities:

| (a) | 34.9 | % NCO | $\eta$ 20° C. = 570 cP |
|---|---|---|---|
| (b) | 32.3 | % NCO | $\eta$ 20° C. = 830 cP |
| (c) | 31.4 | % NCO | $\eta$ 20° C. = 685 cP |

EXAMPLE 21

The following Example shows that mixtures of tolylene-2,4-diisocyanate and tolylene-2,6-diisocyanate in which the ratio of isomers is approximately 65:35 will react readily with catalyst (F) described in Example 13 which carries out preferential carbodiimidization of the 2,4-isomer and converts the mixtures into polyisocyanate mixtures with exceptionally low viscosity in the course of 5 hours at 152° C. Thus, 3132 parts, by weight, of such a mixture of tolyene diisocyanate isomers (18 mol) are reacted with 36 parts, by weight, of a catalyst (F) in the form of beads for 5 hours at 152° C. 112.4 liters of $CO_2$ are evolved and an exceptionally low-viscosity mixture containing about 5 mol of:

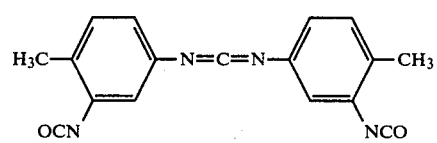

and its triisocyanato uretone imine adduct is obtained. The isocyanate content of the solution is 34.4%, while the viscosity at 20° C. is 8.53 cP.

The product has excellent stability in storage over a tested period of 6 months. It produces no excess $CO_2$ pressure in closed vessels and no increase in viscosity takes place. The equilibrium concentration of uretone imine triisocyanates in the polyisocyanate mixture is almost 70% by weight.

EXAMPLE 22

This Example shows that carbodiimidization catalyst (F) (from Example 13) which is highly active for tolylene diisocyanates is practically completely inert at temperatures of from 150° to 155° C. towards 4,4'-diisocyanatodiphenylmethane, its isomers and solutions thereof in multi-nuclear polyisocyanate mixtures of the type obtained by the phosgenation of commercial aniline-formaldehyde condensates. Within this temperature range, therefore, monoisocyanates and diisocyanates with smaller molecular dimensions can easily be selectively carbodiimized without gel formation in mixtures with such higher molecular weight polyisocyanates.

(a) 1000 parts, by weight, (4 mol) of 4,4'-diisocyanatodiphenylmethane are treated with 12 parts, by weight, of catalyst (F) (from Example 13) for 2 hours at from 148° to 150° C. Virtually no carbodiimide formation takes place. 4,4'-diisocyanatodiphenylmethane crystallizes in practically unchanged form on cooling.

(b) Multi-nuclear polyisocyanate mixtures which have been obtained by the phosgenation of aniline-formaldehyde condensate and have isocyanate contents of from 28 to 33%, by weight, and viscosities of from 100 to 600 cP behave as described under (a).

(c) If from about 5 to 8% of tolylene diisocyanate, phenyl isocyanate or tolyl isocyanate are added to these polyisocyanates under the conditions of experiments (a), these relatively low molecular weight isocyanates are rapidly and selectively carbodiimidized.

(d) When a procedure analogous to that of (a) is carried out, but using the catalyst matrix described in Example 13 (C), which contains basic groups of the constitution:

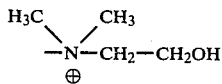

as anchoring groups for the catalyst molecule, carbodiimidization of 4,4'-diisocyanatodiphenylmethane sets in at 150° C. About 0.1 mol of carbodiimide diisocyanate (calculated from the measured quantity of about 4.4 g of $CO_2$) is formed in the course of 1 hour. It is therefore possible by varying the catalysts according to the invention to carry out both selective and simultaneous carbodiimidization reactions in isocyanate mixtures.

EXAMPLE 23

This Example again illustrates that monoisocyanates which have smaller molecular dimensions than tolylene diisocyanate or 4,4'-diisocyanatodiphenylmethane may be converted into carbodiimides much more rapidly and at relatively low temperatures. Carbodiimide formation from tolylene diisocyantes sets in rapidly at about 150° C. when using catalyst (F) (from Example 13), but the smaller molecule of phenyl isocyanate can be rapidly and quantitatively carbodiimidized at from 130° to 132° C., or, in other words at a temperature which is lower by about 20° C.

238 parts, by weight, of phenyl isocyanate (2 mol) are converted into diphenyl carbodiimide with the aid of catalyst (F) at from 128° to 130° C. in the course of 4 hours with evolution of 22.4 l of $CO_2$ (measured at 20° C.). However, even if the diphenyl carbodiimide, which is liquid at 25° C., is obtained in a very pure state, it continues to react after a storage time of about 8 hours to form various adducts or polymerization products, for example, those which have the idealized constitution:

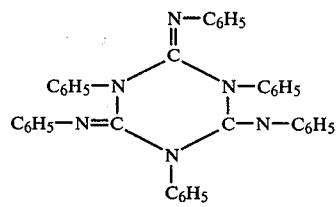

i.e., phenyl imino derivatives of triphenyl isocyanurate, but to some extent it also reacts to form linear polymers of the constitution:

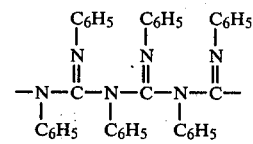

i.e. substituted, basic polyguanidines.

EXAMPLE 24

This Example shows that the less reactive aliphatic and araliphatic diisocyanates, such as hexamethylene diisocyanate and 1-isocyanato-3,3,5-trimethyl-5-isocyanatomethylcyclohexane ("isophorone diisocyanate") may also be converted relatively rapidly into isocyanatocarbodiimides or polyisocyanato-polycarbodiimides and their uretone imines with the aid of the catalysts according to the present invention at elevated temperatures.

(a) 336 g (2 mol) of hexamethylene diisocyanate are partly converted into the compound of the formula:

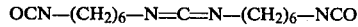

with evolution of 12.6 liters of $CO_2$ in the course of 3 hours at 160° C. with the aid of 4 parts, by weight, of catalyst (C) (from Example 13).

A polyisocyanate mixture with an isocyanate content of 31.4%, by weight, and a viscosity of only 55 cP at 25° C. is obtained. About 0.5 mol of diisocyanato carbodiimide are formed in the reaction. According to IR spectroscopic determinations, at least 70 to 75%, of the diisocyanato carbodiimide continue to react with excess hexamethylene diisocyanate to form uretone imine triisocyanates of the constitution:

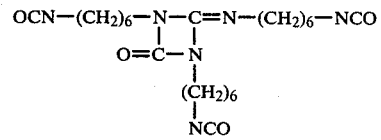

(b) If instead of using the same catalyst as in the previous experiment in the reaction is carried out with 4 parts, by weight, of catalyst (F) which has a more restricted active center, 0.5 mol of:

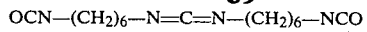

are obtained only after about 5.5 hours and at temperatures of about 180° C. Here again polymerization of the carbodi imides to form polymeric iminocyanurates or polyguanidines is prevented by formation of the uretone imine:

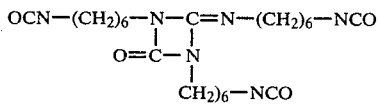

EXAMPLE 25

The cycloaliphatic diisocyanate of the formula:

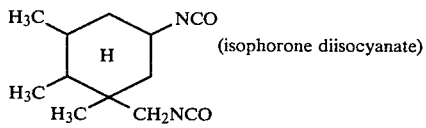
(isophorone diisocyanate)

may also be readily carbodiimidized at from about 160° to 165° C. with the aid of the catalyst (C) from Example 13.

444 parts, by weight, (2 mol) of the cycloaliphatic diisocyanate are reacted with a catalyst mixture of 4 parts, by weight, of (F) and 4 parts, by weight, of (C) for 4 hours at 165° C. 12.2 liters of $CO_2$ are liberated and about 0.5 mol of the compound:

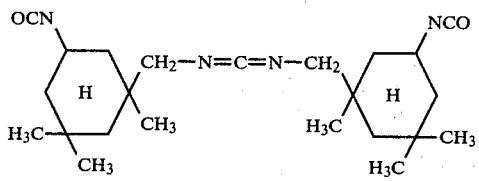

is formed. Isocyanate content of the solution: 25.2%.

In this case again, triisocyanato uretone imine is subsequently formed almost quantitatively so that a solution of about 31 parts, by weight, of triisocyanato uretone imine in about 111 parts, by weight, of isophorone diisocyanate (approximately 73.5%, by weight, solution) is obtained.

EXAMPLE 26

The carbodiimidization of tolylene diisocyanates, 4,4'-diisocyanatodiphenylmethane and any other aromatic diisocyanates may also be continued to produce high molecular weight α,ω-diisocyanatopolycarbodiimides via the stage of diisocyanatocarbodiimides:

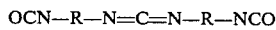

and the stage of triisocyanato uretone imines:

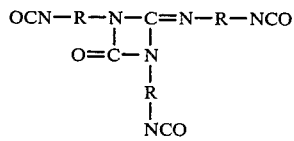

in a solvent-free reaction medium or in solution, in particular with catalyst (C) from Example 13. The powders obtained have a pulverulent consistency. High molecular weight polycarbodiimides of 4,4-diisocyanatodiphenylmethane melt at from 180° to 220° C. and polycarbodiimides of p-phenylene diisocyanate melt at temperatures above 320° C. while α,ω-diisocyanatopolycarbodiimides of the isomeric tolylene diisocyanates begin to soften at from 110° to 140° C. and most of these powders are soluble in methylene chloride. These high molecular weight polycarbodiimides which contain α,ω-isocyanate groups may be prepared in a solvent-free reaction medium or in many cases it is advantageous to use solvents (preferably xylene, ethylene benzene, dimethyl formamide, dimethyl acetamide, tetramethyl urea or tetramethylene sulphone). The isocyanato uretone imines or polyuretone imines formed as intermediate products decompose at 130° C. and are converted quantitatively into polycarbodiimides.

For example, high molecular weight α,ω-diisocyanato-polycarbodiimides are obtained in the form of solid foams which can easily be crushed to powders from:

(a) 2 mol of 4,4'-diisocyanatodiphenylmethane or (b) 2 mol of tolylene-2,4-diisocyanate with the aid of 6 parts, by weight, of catalyst (C) (from Example 13) in each case if the reaction is carried out at from 160° to 180° C. and continued until from about 43 to 44 l of $CO_2$ have been evolved.

When preparing powders which are very difficult to dissolve, for example, from p-phenylene diisocyanate or 4,4'-diisocyanatodiphenylmethane, the catalyst which is in the form of a powder or spherical particles may be left in the polycarbodiimide. When such polycarbodiimides are pressed with exclusion of water, hard, thermoplastic solids are obtained which soften at from 250° to 390° C. and constitute very heat-resistant plastics.

EXAMPLE 27

200 parts, by weight, of (a) a linear adipic acid/ethylene glycol polyester with an OH-number of 67 and (b) a linear polyether of propylene oxide (OH-number 56) are dehydrated in a water jet vacuum at 120° C. for 0.5 hours and in each case converted into the corresponding α,ω-diisocyanato prepolymers by reaction with 85 parts, by weight, (0.34 mol) of 4,4'-diisocyanatodiphenylmethane at 120° C. 34.8 parts, by weight, (0.2 mol) of tolylene-2,4-diisocyanate are then selectively converted into diisocyanatocarbodiimides in these NCO-prepolymers in situ by heating to 150° C. in the presence of 4 g of catalyst (F) (from Example 13), the reaction being accompanied by the evolution of 2.2 g of carbon dioxide. 0.05 mol of the carbodiimide:

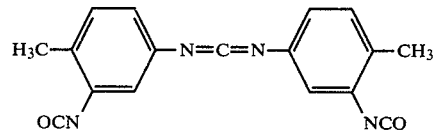

(which partially is convreted into various uretone imine polyisocyanates) is formed in each case. The isocyanate prepolymer mixtures (a') and (b') are dissolved to form 50%, by weight, solutions in dimethylformamide and freed from catalysts by filtration. After the addition of 0.5 parts, by weight, of zinc octoate, the resulting solutions of (a') and (b') harden in air after 24 hours at room temperature when applied as thin layers to metal or wood supports to produce elastic, flexible films in which carbodiimide groups are built into the molecule as chain-lengthening segments.

The chain-lengthening of solutions of the isocyanate prepolymer mixtures (a') and (b') with 0.48 mole of ethylene diamine of 1-amino-3,3,5-trimethyl-5-aminomethylcyclohexane ("isophorone diamine") results in high molecular weight solutions which contain carbodiimide groups. By removal of the solvent, these solutions may be converted into tough, elastic films and coatings which can adhere firmly to any supports, such as paper, textiles, metal sheets or glass.

Chain-lengthening of the 50% solutions (a') and (b') with 0.4 mol of butane diol in 30%, by weight, dimethylformamide solution at 100° C. again gives rise to high molecular weight polyurethanes which contain carbodiimide groups as the chain-lengthening element since the urethane imine groups present are split up by the chain-lengthening reaction.

EXAMPLE 28

200 parts, by weight, of an anhydrous α,ω-dihydroxy propylene glycol polyether which has an OH-number of 56 (average molecular weight 2000) are reacted at 130° C. with 48.4 parts, by weight, of the mixture of isocyanatocarbodIimide and isocyanato uretone imine described in Example 14, (F) which has an isocyanate content of 34.9% and contains about 70%, by weight, of uretone imine polyisocyanate of the following constitution:

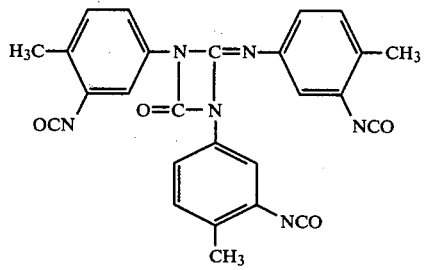

Owing to the ease with which isocyanato uretone imines decompose at 130° C., the reaction results in isocyanate prepolymers which, represented ideally, contain isocyanato-carbodiimide groups of the following formula:

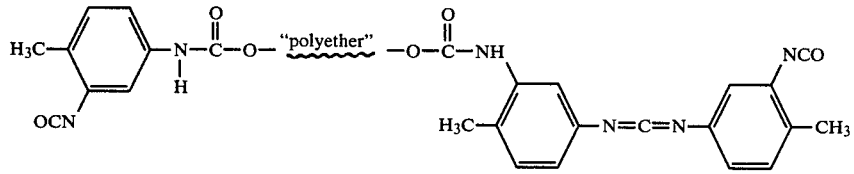

When the prepolymers are applied as thin layers to glass, metal or wood surfaces, they react with the atomspheric moisture to form polyureas which contain carbodiimide groups as chain-lengthening segments and change into highly elastic films.

EXAMPLE 29

This Example illustrates how the solutions according to the invention which contain diisocyanatocarbodiimides or isocyanato uretone imines react smoothly to form elastic foams which contain, built into the molecule, carbodiimide groups or uretone imine groups as masked carbodiimides.

100 parts, by weight, of a polypropylene glycol ether which has been prepared from trimethylolpropane and 1,2-propylene glycol (1:1) as starting components (OH-number 47), 2.7 parts, by weight, of water, 0.8 parts, by weight of a commerical foam stabilizer based on a polyetherpolysiloxane copolymer, 0.1 part, by weight, of permethylated diethylene triamine and 0.23 parts, by weight of a tin-(II) salt of 2-ethyl caproic acid are mixed together. 63.5 parts, by weight, of the mixture according to the invention from Example 14 (F) which has an isocyanate content of 34.9 % are added and the components are vigorously mixed with the aid of a high-speed stirrer. The white, elastic foam obtained has a substantially open-celled structure and a density of about 39 kg/m³.

What is claimed is:

1. A composition of matter comprising a storage-stable, catalyst-free, equilibrium mixture of an organic carbodiimide, an organic uretone imine, and an organic isocyanate produced by the process comprising:
   (a) contacting an organic mono- and/or polyisocyanate, optionally dissolved in an inert solvent, with a high molecular weight, insoluble catalyst, said catalyst comprising a high molecular weight, insoluble inorganic or organic matrix and a low molecular weight carbodiimidization catalyst linked to said matrix via ionic bonds, and
   (b) removing said insoluble catalyst when the desired degree of carbodiimidization has been reached.

2. The composition of claim 1, wherein at least one of said carbodiimide or said uretone imine contains isocyanate groups.

3. The composition of claim 2, wherein said isocyanate is a mono and/or polyisocyanate free from carbodiimide and uretone imine groups.

4. The composition of claim 1, wherein said isocyanate is a mono and/or polyisocyanate free from carbodiimide and uretone imine groups.

5. The composition of claim 4 comprising
   (A) an equilibrium mixture of (i) the diisocyanatocarbodiimide of tolylene diisocyanate, and (ii) the corresponding triisocyanato uretone imine, and
   (B) an isocyanate selected from the group consisting of 4,4'-diisocyanatodiphenylmethane, naphthylene-1,5-diisocyanate, and mixtures thereof.

6. The composition of claim 5 wherein component (A) comprises from about 5 to about 80 parts, by weight, and component (B) comprises about 100 parts by weight.

7. The composition of claim 4 comprising:
   (A) an equilibrium mixture of the carbodiimide and uretone imine of a member selected from the group consisting of phenyl isocyanate, hexamethylene diisocyanate, tetramethylene diisocyanate, cyclohexyl isocyanate and tolyl isocyanate, and (B) an isocyanate selected from the group consisting of 4,4'-diisocyanatodiphenylmethane, naphthylene-1,5-diisocyanate, and mixtures thereof.

8. The composition of claim 7, wherein component (A) comprises from about 10 to about 30 parts by weight and component (B) comprises about 100 parts by weight.

9. The composition of claim 4 comprising:
(A) an equilibrium mixture of the carbodiimide and uretone imine of a member selected from the group consisting of phenyl isocyanate and tolyl isocyanate, and
(B) tolylene diisocyanate.

10. The composition of claim 9, wherein component (A) comprises from about 5 to about 30 parts by weight, and component (B) comprises about 100 parts by weight.

11. The composition of claim 4 comprising:
(A) an equilibrium mixture of the carbodiimide and uretone imines of tolylene diisocyanate, and
(B) a modified tolylene diisocyanate containing from about 10 to about 40 percent by weight of biuret, allophanate, urethane or isocyanurate polyisocyanates based on tolylene diisocyanate.

12. The composition of claim 11, wherein component (A) comprises from about 10 to about 20 parts by weight, and component (B) comprises about 100 parts by weight.

13. The composition of claim 4 comprising:
(A) an equilibrium mixture of the carbodiimide and uretone imines of hexamethylene diisocyanate, and
(B) the biuret polyisocyanates of hexamethylene diisocyanates.

14. The composition of claim 13, wherein component (A) comprises from about 10 to about 30 parts by weight, and component (B) comprises about 100 parts by weight.

15. The composition of claim 4 comprising:
(A) an equilibrium mixture of the carbodiimide and uretone imines of a member selected from the group consisting of phenyl isocyanate, tolyl isocyanate, tetramethylene diisocyanate, hexamethylene diisocyanate, and tolylene diisocyanate; and
(B) α, ω-diisocyanato prepolymers derived from 1 mol of α,ω-dihydroxy polyesters or polyethers having molecular weights of from about 400 to about 10,000, and from about 1.4 to about 2.5 mole of an isocyanate selected from the group consisting of tolylene diisocyanate, diisocyanatodiphenylmethane, and hexamethylene diisocyanate.

16. The composition of claim 15, wherein component (A) comprises from about 5 to about 30 parts by weight, and component (B) comprises about 100 parts by weight.

17. The composition of claim 1, wherein the process further comprises the step of: adding a mono- or polyisocyanate which is free from carbodiimide and uretone imide groups to the equilibrium mixture.

18. A process for preparing a storage stable, catalyst-free, equilibrium mixture of an organic carbodiimide, an organic uretone imine, and an organic isocyanate comprising the steps:
(A) contacting an organic mono and/or polyisocyanate, optionally dissolved in an inert solvent, with a high molecular weight, insoluble catalyst, said catalyst comprising a high molecular weight, insoluble, inorganic or organic matrix and a low molecular weight carbodiimidization catalyst linked to said matrix via ionic bonds, and
(B) removing said insoluble catalyst when the desired degree of carbodiimidization has been reached.

19. The process of claim 18, further comprising the step of
(C) adding a mono and/or polyisocyanate which is free from carbodiimide and uretone imine groups to the equilibrium mixture.

* * * * *